(12) United States Patent
Knochel et al.

(10) Patent No.: US 9,273,070 B2
(45) Date of Patent: Mar. 1, 2016

(54) ORGANOZINC COMPLEXES AND PROCESSES FOR MAKING AND USING THE SAME

(76) Inventors: Paul Knochel, Munich (DE); Sebastian Bernhardt, Munich (DE); Georg Manolikakes, Frankfurt am Main (DE)

( * ) Notice: Subject to any disclaimer, the term of this patent is extended or adjusted under 35 U.S.C. 154(b) by 215 days.

(21) Appl. No.: 13/996,953

(22) PCT Filed: Dec. 21, 2011

(86) PCT No.: PCT/EP2011/073714
§ 371 (c)(1),
(2), (4) Date: Oct. 14, 2013

(87) PCT Pub. No.: WO2012/085168
PCT Pub. Date: Jun. 28, 2012

(65) Prior Publication Data
US 2014/0031545 A1  Jan. 30, 2014

Related U.S. Application Data

(60) Provisional application No. 61/425,824, filed on Dec. 22, 2010.

(51) Int. Cl.
*C07F 3/06* (2006.01)
*C07F 7/08* (2006.01)
(Continued)

(52) U.S. Cl.
CPC . *C07F 3/06* (2013.01); *C07B 37/04* (2013.01); *C07C 67/343* (2013.01);
(Continued)

(58) Field of Classification Search
CPC .......... C07F 3/06; C07F 7/083; C07F 7/1892; C07B 37/04; C07C 67/343; C07C 231/12; C07C 253/30; C07D 213/84; C07D 213/85; C07D 215/12; C07D 239/52
USPC ........... 556/12, 123, 124, 126, 130, 131, 417, 556/436; 544/225, 311, 314; 546/4, 173; 558/378; 560/37, 102
See application file for complete search history.

(56) References Cited

U.S. PATENT DOCUMENTS

2008/0262256 A1* 10/2008 Herrmann et al. ............... 556/46
2010/0144516 A1   6/2010 Clososki et al.
(Continued)

OTHER PUBLICATIONS
Sobota et al., New J. Chem., vol. 24, pp. 523-526 (2004).*
(Continued)

*Primary Examiner* — Porfirio Nazario Gonzalez
(74) *Attorney, Agent, or Firm* — Stolmar & Partner; Robert Lelkes

(57) ABSTRACT

Processes for making an organozinc reagents are disclosed comprising reacting (A) organomagnesium or organozinc complexes with (B) at least one coordination compound comprising one or more carboxylate groups and/or alcoholate groups and/or tertiary amine groups, optionally in combination with zinc ions and/or lithium ions and/or halide ions, wherein the halide ions are selected from chloride, bromide and iodide, the organozinc complex comprises an aryl group, a heteroaryl group or a benzyl group when the coordinating compound is a chelating polyamine, and the reaction is conducted in the presence of zinc complexed with at least one coordinating compound when reactant (A) comprises at least one organomagnesium complex. The resulting organozinc reagents may optionally be isolated from solvents to obtain a solid reagent. The reagents may be used for making organic compounds via Negishi cross-coupling reactions or via aldehyde and/or ketone oxidative addition reactions. The organozinc reagents are stable and, due to their high selectivity, permit maintenance of sensitive functional groups such as aldehydes during cross-coupling.

19 Claims, 1 Drawing Sheet

(51) Int. Cl.
- C07F 7/18 (2006.01)
- C07C 67/343 (2006.01)
- C07B 37/04 (2006.01)
- C07C 231/12 (2006.01)
- C07C 253/30 (2006.01)
- C07D 213/84 (2006.01)
- C07D 213/85 (2006.01)
- C07D 215/12 (2006.01)
- C07D 239/52 (2006.01)

(52) U.S. Cl.
CPC ............ *C07C 231/12* (2013.01); *C07C 253/30* (2013.01); *C07D 213/84* (2013.01); *C07D 213/85* (2013.01); *C07D 215/12* (2013.01); *C07D 239/52* (2013.01); *C07F 7/083* (2013.01); *C07F 7/1892* (2013.01)

(56) References Cited

U.S. PATENT DOCUMENTS

| | | |
|---|---|---|
| 2010/0160632 A1 | 6/2010 | Knochel et al. |
| 2011/0084230 A1 | 4/2011 | Knochel et al. |

OTHER PUBLICATIONS

Jana et al., Dalton Transactions, Issue 9, pp. 1516-1521 (2009).*
Metzger et al., Angew. Chem. Int. Ed., vol. 49, pp. 4665-4668 (Published online: May 17, 2010).*
Wunderlich et al., Angew. Chem. Int. Ed., vol. 46, pp. 7685-7688 (2007).*
Bernhardt et al., Angew. Chem. Int. Ed., vol. 50, pp. 9205-9209 (2011).*
Piller et al., Chem. Eur. J., vol. 15, pp. 7192-7202 (2009).*
Mosrin et al., Organic Letters, vol. 11, No. 8, pp. 1837-1840 (2009).*
Mosrin et al., Organic Letters, vol. 11, No. 15, pp. 3406-3409 (2009).*
Alexander J. Blake, et al., A zinc—lithium complex of 4,7-bis-(2-aminoethyl)-1,4,7-triazacyclo-nonane-1-acetate, Acta Cryst. (2003). C59, m43-m45.
Tobias D. Blümke, et al., Preparation of highly functionalized alkylzinc halides from alkyl bromides using Mg, ZnCl2 and LiCl, Chem. Commun., 2010, 46, 4082-4084.
Tobias Blümke, et al., Preparation of functionalized organoaluminiums by direct insertion of aluminium to unsaturated halides, Nature Chemisty, vol. 2, Apr. 2010, p. 313-318.
Nadège Boudet, et al., Directed Ortho Insertion (DoI): A New Approach to Functionalized Aryl and Heteroaryl Zinc Reagents, J. Am. Chem. Soc., 2007, 129, 12358-12359.
Ross Campbell, et al., Synergic Transformation of an Ethylenediamine to a Lithium 1,3-Diaza-2-zincacyclopentene via an Alkyllithium/Bis(alkyl)zinc Mixture, Chem. Eur. J., 2010, 16, 9964-9968.
Ina Hegelmann, et al., Alkylzinc Complexes with Achiral and Chiral Monoanionic N,N,O Heteroscorpionate Ligands, Eur. J. Inorg. Chem., 2003, 339-347.
Hiriyakkanavar Ila, et al., Preparation and Reactions of Heteroaryl Organomagnesium Compounds, Chemistry Letters vol. 34, No. * (2005).
Hiriyakkanavar Ila, et al., Functionalized magnesium organometallics as versatile intermediates for the synthesis of polyfunctional heterocycles, Chem. Commun., 2006, 583-593.
Cameron Jones, et al., Bulky guanidinato and amidinato zinc complexes and their comparative stabilities, Dalton Trans., 2010, 39, 8788-8795.
Marcel Kienle, et al., i-PrI Acceleration of Negishi Cross-Coupling Reactions, Org. Lett., 2010, vol. 12, No. 12, 2702-2705.
Arkady Krasovskiy, et al., Efficient Synthesis of Functionalized Organozinc Compounds by the Direct Insertion of Zinc into Organic Iodides and Bromides, Angew. Chem. Int. Ed. 2006, 45, 6040-6044.
Wenwei Lin, et al., Highly Functionalized Benzene Syntheses by Directed Mono or Mutiple Magnesiations with TMPMgCl-LiCl, Org. Lett., published on Web Nov. 3, 2006, pp. A-D.
Albrecht Metzger, et al., Polyfunctional benzylic zinc chlorides by the direct insertion of magnesium into benzylic chlorides in the presence of LiCl and ZnCl2, Chem. Commun., 2008, 5824-5826.
Albrecht Metzger, et al., LiCl-Mediated Preparation of Highly Functionalized Benzylic Zinc Chlorides, Organic Letters, 2008, vol. 10, No. 6, 1107-1110.
Fabian M. Piller, et al., Convenient Preparation of Polyfunctional Aryl Magnesium Reagents by a Direct Magnesium Insertion in the Presence of LiCl, Angew. Chem. Int. Ed. 2008, 47,6802-6806.
R. R. Rakhimov, et al., Structure of Orthosemiquinone Complexes of Zinc and Cadmium Chloride, Plenum Publishing Corporation, 1989, 999-1000.
Paul Knochel, et al., Functionalization of heterocyclic compounds using polyfunctional magnesium and zinc reagents, Beilstein J. Org. Chem., 2011, 7, 1261-1277.
Paul Knochel, The Salt in the Chemical Soup—A new path to catalytic organometallics, Sep. 23, 2008, https://www.en.uni-muenchen.de/news/newsarchiv/2008/knochel.html.
Michael J. S. Dewar, et al., The Reformatsky Reaction, J. Am. Chem. Soc., 1987, 109, 6553-6554.
Benjamin W. Gung, et al., Addition of Chiral Allenylzinc Reagent to Acetaldehyde: Diastereotopic Cyclic Transition States with a Tetrahedral Zinc Atom Located by ab Initio and Density Functional Theory, Organometallics, 2003, 3158-3163.
Harry L. Anderson, Conjugated Porphyrin Ladders, Inorg. Chem., 1994, 33, 972-981.
Jan Dekker, et al., The Nature of the Reformatsky Reagent. Crystal Structure of (BrZnCH2COO-t-Bu-THF)2, Organometallics, 1984, 3, 1403-1407.
Wolfgang Hörner, EXAFS investigation of metal organic synthesis tools, Journal of Organometallic Chemistry, 649, 2002, 128-135.
Jan Dekker, et al., The Structure of the Reformatsky Reagent, J. Chem. Soc., Chem. Commun., 1983, 553-555.
Wen-Jian Liu, et al. Progress in Asymmetrically Catalyzed Addition of Organozinc Reagents to Ketones, Chinese Journal of Organic Chemistry, 2008, 28, 1348-1357.

* cited by examiner

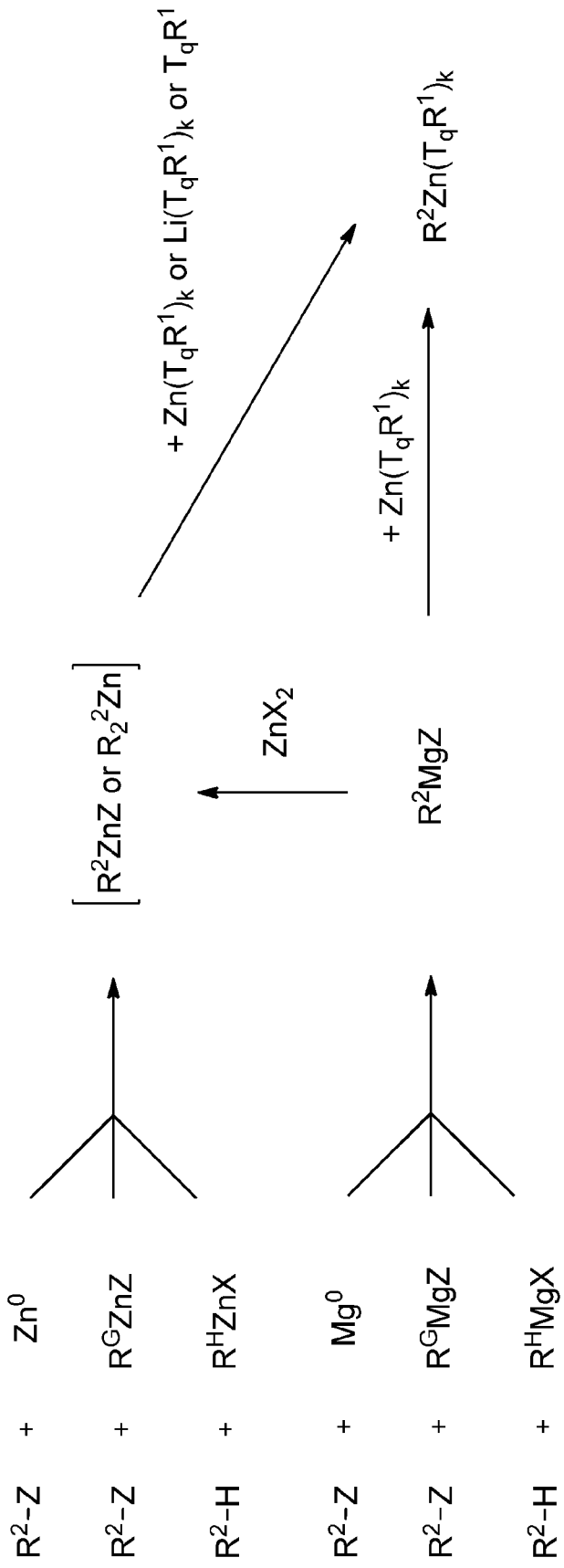

ORGANOZINC COMPLEXES AND PROCESSES FOR MAKING AND USING THE SAME

FIELD OF THE INVENTION

The present invention relates to organozinc reagents and their use in cross-coupling reactions, particularly in Negishi-couplings.

BACKGROUND OF THE INVENTION

Transition metal-catalyzed cross-coupling reactions of organometallics are key transformations in organic synthesis. Their broad spectrum of applications ranges from the synthesis of small molecular units to the construction of organic materials and complex natural products. Besides Kumada-Corriu-coupling, the Suzuki-Miyaura-, and the Negishi-cross-coupling reactions are of great importance in various chemical and pharmaceutical manufacturing applications.

Organozinc reagents used in Negishi-couplings can be prepared in a convenient and cheap way by direct oxidative addition of zinc metal into organic halides. Various functionalized aryl, heteroaryl and benzylic zinc reagents are accessible via such cross-coupling reactions in good yields. Cross-coupling reactions with zinc organometallics can be performed under mild conditions and in good yields with a broad spectrum of electrophiles. Consequently, organozinc reagents are of considerable interest for industrial applications. They can be stored as solutions in THF under inert gas atmosphere for several weeks without significant loss of activity.

However, it would be advantageous in terms of storage as well as transportation and manipulation on an industrial scale to use organozincs as solid materials. So far, zinc reagents of the composition RZnX, RZnX.LiCl and RZnX.MgCl$_2$.LiCl (R=aryl, heteroaryl, benzyl, alkyl and X=Cl, Br, I) have only been obtained as highly viscous oils after the evaporation of the solvent and have therefore not been available as solids.

There is also a desire to increase the selectivity of cross-coupling reactions to allow sensitive functional groups such as ester, aldehyde, nitrile and nitro to be present in the electrophiles.

The invention disclosed herein addresses this and other shortcomings in metalated reagents suitable for use in commercial-scale cross-coupling reactions as further described and disclosed below.

SUMMARY OF THE INVENTION

One aspect of the invention described herein is a process for making organozinc reagents comprising reacting (A) at least one organomagnesium complex or organozinc complex with (B) at least one coordinating compound comprising one or more carboxylate groups and/or alcoholate groups and/or tertiary amine groups, optionally in combination with zinc ions and/or lithium ions and/or halide ions, wherein the halide ions are selected from chloride, bromide and iodide, the organozinc complex comprises an aryl group, a heteroaryl group or a benzyl group when the coordinating compound is a chelating polyamine, and the reaction is conducted in the presence of zinc complexed with at least one coordinating compound when reactant (A) comprises at least one organomagnesium complex.

A further aspect of the invention is a process for making organozinc reagents comprising contacting an organic compound having at least one leaving group with magnesium metal and a zinc coordination complex optionally in the presence of lithium halide, wherein the halide is selected from chloride, bromide and iodide and the zinc coordination complex comprises at least one coordinating compound comprising one or more carboxylate groups and/or alcoholate groups and/or tertiary amine groups.

Yet a further aspect of the invention is a process for making organozinc reagents comprising reacting (A) at least one organozinc compound with (B) at least one coordinating compound comprising one or more carboxylate groups and/or alcoholate groups and/or tertiary amine groups, optionally in combination with zinc ions and/or lithium ions and/or halide ions, wherein the halide ions are selected from chloride, bromide and iodide.

Another aspect of the invention is a process for making an organozinc reagent comprising complexing, such as via contacting, at least one organomagnesium complex or organozinc complex with at least one coordinating compound and optionally evaporating the solvent to obtain a solid organozinc reagent, wherein the coordinating compound preferably comprises one or more carboxylate groups and/or alcoholate groups and/or tertiary amine groups.

Another aspect of the invention described herein is a zinc coordination complex comprising zinc ions, at least one coordinating compound comprising one or more carboxylate groups and/or alcoholate groups and/or tertiary amine groups, lithium ions, and halide ions, wherein the halide is chloride, bromide or iodide.

A further aspect of the invention described herein is organozinc reagent compositions comprising (a) at least one organozinc compound complexed with at least one coordinating compound comprising one or more carboxylate groups and/or alcoholate groups and/or tertiary amine groups, (b) optionally magnesium ions, optionally (c) lithium ions, and optionally (d) halide ions, wherein the halide is selected from chloride, bromide and iodide and the organozinc compound comprises an aryl group, a heteroaryl group or a benzyl group when the coordinating compound is a chelating polyamine.

Yet a further aspect of the invention described herein is a process for making organic compounds comprising reacting nucleophilic leaving group substituted organic compounds (i.e., electrophiles) with at least one organozinc reagent comprising (a) at least one organozinc compound, (b) at least one coordinating compound comprising one or more carboxylate groups and/or alcoholate groups and/or tertiary amine groups, (c) optionally magnesium ions, (d) optionally lithium ions, optionally halide ions, wherein the halide is selected from chloride, bromide and iodide, and (e) at least one cross-coupling catalyst to form organic compounds via cross-coupling.

A still further aspect of the invention described herein is a process for making organic compounds comprising reacting an aldehyde- and/or ketone-substituted organic compound with an organozinc reagent comprising (a) at least one organozinc compound, (b) at least one coordinating compound comprising one or more carboxylate groups and/or alcoholate groups and/or tertiary amine groups, optionally magnesium ions, optionally lithium ions and optionally halide ions, wherein the halide is selected from chloride, bromide or iodide, in the absence of a cross-coupling catalyst to form the organic compound via an aldehyde and/or ketone addition reaction.

The organozinc reagent may be reacted with nucleophilic leaving group substituted organic compounds (i.e., electrophiles) in the presence of a cross-coupling catalyst to form organic compounds via cross-coupling or the organozinc reagent may be reacted with an aldehyde- and/or ketone-substituted organic compound in the absence of a cross-coupling catalyst to form organic compounds via an aldehyde and/or ketone addition reaction.

Each aspect of this invention is described in more detail in the following section and in the appended claims, which are incorporated herein by reference.

BRIEF DESCRIPTION OF THE DRAWING

The drawing, identified as "FIGURE", shows some reaction pathways according to the present invention in a schematic form based on the generic definitions for the $R^1$, $R^2$, T, X, Z, q, and k groups given in the following detailed description of the invention. Certain details regarding mass balance, salt ions and byproducts are not shown to simplify the schematic presentation.

DETAILED DESCRIPTION OF THE INVENTION

Definitions

Definitions for expressions and abbreviations used herein are provided below:

"AcOEt" means "ethyl acetate".

"Boc" means "tert-butoxycarbonyl".

"Chelating polyamine", as used herein, means an organic moiety having two or more tertiary amine groups capable of coordinating with zinc ions to form coordination compound or complex with zinc ions by donating a pair of electrons per nitrogen atom. Chelating polyamines are multidentate, such as bidentate, tridentate or tetradentate.

"Coordinating compound", as used herein, means a compound that forms a complex, or coordination compound, with zinc ions via at least one ligand. The coordinating compound is preferably a Lewis base, wherein the electron donor atoms are preferably selected from N, P, O and S. The coordinating compound may be monodentate or multidentate, such as bidentate, tridentate, tetradentate, etc. When the coordinating compound comprises one or more alcoholate groups and/or tertiary amine groups, the coordinating compound in one embodiment may preferably form a chelate complex via a multidentate ligand, such as a bidentate ligand, with a zinc ion, such as 1,2-ligands. Preferred coordinating compounds comprising tertiary amines include polyamines, including diamines, and more preferably including aliphatic diamines such as TMEDA (see definition below).

"DMSO" refers to "dimethyl sulfoxide", which may be used as a coordinating compound.

"HMDS" refers to "hexamethyldisilazide".

"ihexane" refers to a mixture of hexane isomers used in liquid chromatography.

"iPr" refers to an isopropyl group.

"Me" refers to a "methyl group".

"Me-THF" refers to "2-methyltetrahydrofuran", which may be used as a solvent.

"NMP" refers to "N-methyl-2-pyrrolidone", which may be used as a solvent.

"OPiv" refers to "pivalate" coordinated with a metal ion, such as a zinc or magnesium ion, via the pivalate carboxylate group.

"Organomagnesium complex" means an organic compound having a magnesium atom directly bonded to, or coordinated with, a carbon atom of the organic compound via metal coordination complex bonding. This expression includes the optional presence of coordinating compounds, preferably Lewis bases, and optional ions such as Li ions, Mg ions, and halide ions.

"Organozinc complex" and "organozinc compound" refer to an organic compound having at least one zinc atom directly bonded to, or coordinated with, a carbon atom of an organic compound (Zn<-C) via metal coordination complex bonding. The expression "organozinc compound" refers solely to the organozinc moiety and may be cationic or neutral, whereas the expression "organozinc complex" includes the optional presence of ions, such as Li ions, Mg ions, and halide ions, and coordinating compounds. The expression "organozinc complex" preferably does not include the coordinating compounds of the organozinc reagent.

"PEPPSI™-iPr" refers to "Pyridine-Enhanced Precatalyst Preparation Stabilization and Initiation", a palladium N-heterocyclic-carbene (NHC) catalyst system developed by Professor Mike Organ at York University, along with co-workers Dr. Chris O'Brien and Dr. Eric Kantchev (Organ, M. G., Rational catalyst design and its application in $sp^3$-$sp^3$ couplings, presented at the 230th National Meeting of the American Chemical Society, Washington, D.C., 2005; Abstract 308) having the formula [1,3-Bis(2,6-Diisopropylphenyl) imidazol-2-ylidene](3-chloropyridyl)palladium(II)dichloride and having the chemical structure:

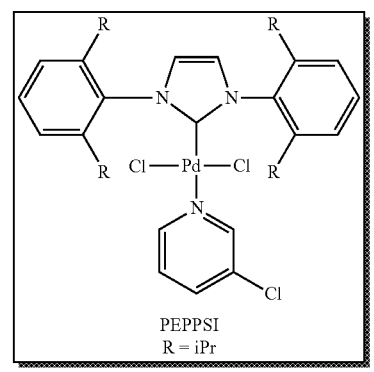

This catalyst may be obtained from Sigma Aldrich.

"Pivalate" refers to "trimethylacetate", also known as "2,2-dimethylpropanoate" or "trimethylacetic acid".

"Pr" refers to a "propyl" group.

"S-Phos" refers to 2-dicyclohexylphosphino-2',6'-dimethoxybiphenyl.

"tert-butylate" as used herein refers to 2-methyl-2 propanolate (also known as tert-butanolate and tert-butoxide).

"THF" refers to the solvent "tetrahydrofuran", which may be used as a solvent.

"TIPS" refers to "triisopropylsilyl", which may be used as a protecting group for protecting alcohols.

"TMEDA" refers to "N,N,N',N'-tetramethylethane-1,2-diamine", also known as tetramethylethylenediamine", i.e., $(CH_3)_2NCH_2CH_2N(CH_3)_2$, a coordinating solvent.

"TMP" refers to "2,2,6,6-tetramethylpiperidyl", a coordinating amide.

Zinc alcoholate complex means that one or more zinc ions are complexed, or coordinated, with one or more organic compounds having one or more alcoholate groups via the alcoholate ($O^-$) group.

Zinc carboxylate complex means that one or more zinc ions are complexed, or coordinated, with one or more organic compounds having one or more carboxylate groups via the carboxylate groups.

Zinc tertiary amine complex means that one or more zinc ions are complexed, or coordinated with one or more organic compounds having one or more tertiary amine groups via an unbonded pair of electrons of one or more amine nitrogen atoms.

Zinc Coordination Complexes

In the process for making the organozinc reagent according to the invention, an organomagnesium complex may be reacted with a zinc coordination complex. The coordination complex comprises at least one zinc ion and at least one coordinating compound comprising one or more carboxylate groups and/or alcoholate groups and/or tertiary amine groups. The coordinating compound is preferably represented by the formula (I):

$$R^1T_q \qquad (I)$$

wherein
each T independently represents $-CO_2^-$, $-O^-$, or $-NR'R''$, wherein each R' and R'' independently represent a hydrocarbyl group having from 1 to 6 carbon atoms, wherein the hydrocarbyl group is preferably selected from methyl, ethyl, n-propyl, isopropyl, n-butyl, sec-butyl, and tert-butyl, more preferably methyl, which may optionally further comprise one or more hetero atoms, such as O, N, or S atoms, wherein the hetero atoms are preferably not protonated, and R' and R'' may be joined together to form a substituted or unsubstituted five- or six-membered heterocyclic ring with the nitrogen atom of $-NR'R''$;
$R^1$ represents an organic residue comprising one or more carbon atoms and, optionally, one or more hetero atoms, wherein the organic residue preferably does not comprise protonated O, N, or S and preferably does not comprise T; and "q" represents a positive integer, wherein the integer is preferably at least 1, in some embodiments more preferably at least 2, up to 6, more preferably up to 4, even more preferably up to 3, even more preferably up to 2 and, in some embodiments, yet more preferably q is equal to 1. When T represents $-O^-$ or $-NR'R''$, "q" is, in some embodiments, preferably at least 2.

When q is 2 or more, the minimum number of atoms of $R^1$ linking each T to the next adjacent T of Formula (I) via covalent bonds is preferably at least 1, more preferably at least 2, and the maximum number of atoms of $R^1$ linking T to the next adjacent T of Formula (I) via covalent bonds is preferably 6, more preferably 4, even more preferably 3, and even more preferably 2. The intervening linking atoms are preferably carbon atoms and the referenced covalent bonds are preferably saturated covalent bonds.

$R^1$ preferably comprises one or more cyclic groups and/or one or more aliphatic groups.

The cyclic groups may comprise carbocyclic groups, such as cycloalkyl groups and aryl groups, and heterocyclic groups, such as heteroaryl groups and partially or fully saturated heterocyclic compounds. Preferred cyclic groups have at least 4, more preferably at least 5, and even more preferably at least 6, up to 20, more preferably up to 15, and even more preferably up to 10, carbon atoms and optionally from 1 preferably up to a number of hetero atoms equal to the number of carbon atoms in the cyclic group. The heteroatoms are preferably selected from B, O, N, S, Se, P and Si, and more preferably selected from O, N and S. The cyclic group may comprise a monocyclic or polycyclic ring system. The polycyclic ring system may comprise fused ring systems, bridged ring systems and rings having one atom in common.

The aliphatic group preferably comprises at least 2, more preferably at least 3, and even more preferably at least 4, up to 20, more preferably up to 12, and even more preferably up to 8, and even more preferably up to 6, carbon atoms. The aliphatic group may be straight-chained or branched, may comprise one or more heteroatoms representing up to half, more preferably up to one-fourth, the total number of atoms in the aliphatic group, and may comprise one or more unsaturated bonds. The heteroatoms are preferably selected from B, O, N, S, Se, P and Si, and more preferably selected from O, N and S. The unsaturated bonds are preferably double bonds and triple bonds. Preferred aliphatic groups include alkyl groups, alkenyl groups and alkynyl groups. The aliphatic groups may preferably be saturated (i.e., do not contain unsaturated bonds).

The substituents are preferably selected from among the aforementioned preferred $R^1$ cyclic and aliphatic groups, F, and nonprotonated functional groups.

In a preferred embodiment, $R^1$ represents a straight or branched alkyl group having at least 4, and preferably up to 8, carbon atoms. In a particularly preferred embodiment, $R^1$ is $-C(CH_3)_3$ (i.e., tert-butyl), T is preferably carboxylate or alcoholate, and/or q is preferably 1, so that the anions of Formula (I) are preferably pivalate and/or 2-methyl-2 propanolate (also known as tert-butanolate, tert-butylate and tert-butoxide) and/or lactate.

Thus, preferred zinc coordination complexes may be generically represented by the Formula (IA):

$$R^1T^*Zn^*TR^1 \qquad (IA)$$

wherein T and $R^1$ are defined as in Formula (I).

To facilitate the reaction with the organomagnesium complex, the zinc coordination complex preferably comprises lithium halide, wherein the halide is preferably Cl, Br or I, and most preferably Cl. The lithium halide salt complex may be obtained by deprotonating the acid or alcohol corresponding to the above-described carboxylate or alcoholate exemplified by Formula (I) with methyllithium in THF and then transmetalating the deprotonated acid or alcohol with a zinc halide, wherein the halide is the halide desired for the lithium halide (e.g., Cl if the LiCl salt complex is desired). This reaction is illustrated in more detail in the description of the preparation of the zinc pivalate complex 2a and the zinc tert-butylate complex 2b in the examples below.

The resulting preferred lithium salt complex comprises units that may be represented by Formula (IB):

$$Zn(T_qR^1)_k \qquad (IB)$$

wherein T, $R^1$ and q have the same meaning, including preferred meanings, as in Formula (I) and k represents a positive integer corresponding to the number of units of $T_qR^1$ coordinated with Zn. Subscript k is preferably in the range from 1 to 3, more preferably 2. In a preferred embodiment, q is 1 and k is equal to 2. The units of Formula (IB) may be neutral or have a negative charge depending on the nature and number of T groups. Charged units of Formula (IB) may be compensated by cations in a lithium salt complex composition.

The lithium complex preferably comprises LiX, wherein X represents Cl, Br or I.

Lithium Coordination Complexes

In the process for making the organozinc reagent according to the invention, an organozinc complex may be reacted with a lithium coordination complex. The lithium coordination complex comprises at least one lithium ion and at least one coordinating compound comprising one or more carboxylate groups and/or alcoholate groups and/or tertiary amine groups. The coordinating compound is preferably represented by the formula $R^1T$, wherein $R^1$ and T have the same meaning as defined above for formula (I), including the preferred meanings.

Preferred lithium coordinating compounds may thus be generically represented by the Formula (IC):

$$Li^*(T_qR^1)_k \qquad (IC)$$

wherein T, $R^1$, q and k are defined as in Formula (I), wherein q and k are each preferably equal to an integer in the range from 1 to 3, more preferably the integer 1 or 2, and q+k is preferably equal to 1 or 2. $R^1T_q$ is preferably a carboxylate or alcoholate, more preferably a carboxylate, and even more preferably lactate or pivalate, and yet more preferably pivalate. The units of Formula (IC) may be neutral, have a negative charge or have a positive charge depending on the nature and number of T groups. Charged units of Formula (IC) may be compensated by cations or anions in a lithium salt complex composition.

The organozinc complex may comprise one or more functional groups, such as the functional groups that may be present in the organomagnesium complex described below. In particular, the functional groups may comprise groups such as nitriles, nitro, esters, ketones, protected alcohols, protected aldehydes, protected amines and protected amides.

Organomagnesium Complex

The organomagnesium complex is an organic compound metalated with Mg. Metalation may by conducted by (1) reacting an organic compound having at least one leaving group with magnesium metal to insert a magnesium atom via oxidative addition, (2) halogen-magnesium exchange, or (3) C—H activation.

Oxidative addition may be conducted in accordance with the following scheme:

$$R^2Z + Mg^0 \rightarrow R^2MgZ \quad \text{(IIA)},$$

halogen-magnesium exchange may be conducted in accordance with the following scheme:

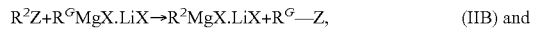

$$R^2Z + R^GMgX \cdot LiX \rightarrow R^2MgX \cdot LiX + R^G\text{—}Z, \quad \text{(IIB) and}$$

C—H activation may be conducted in accordance with the following scheme:

$$R^2H + R^HMgX \rightarrow R^2MgX + R^H\text{—}H \quad \text{(IIC)}$$

in which LiX may be present and may be coordinated with MgX of $R^HMgX$, wherein $R^2$ is an organic moiety, $R^G$ represents a hydrocarbyl group preferably having from 1 to 12 carbon atoms, more preferably having up to 8 carbon atoms, such as an alkyl group, an aryl group, or an aralkyl group, which may be optionally substituted with one or more, preferably up to 4, more preferably up to two, hydrocarbyl groups, such as alkyl groups, aryl groups and aralkyl groups, having from 1 to 12 carbon atoms, more preferably from 1 to 8 carbon atoms, $R^H$ represents an amide moiety, each X independently represents a halide selected from Cl, Br, and I, and Z is a leaving group. Preferred hydrocarbyl groups, $R^G$, include hydrocarbyl groups in which the total number of carbon atoms, including substituents, is in the range from 3 to 12, more preferably in the range from 3 to 8, such as iPr, sec-butyl, bis-sec-butyl and bis-iPr. Preferred amide moieties, $R^H$, include diisopropylamide, tmp, and HMDS. Preferred leaving groups Z are Cl, Br, I, triflate, mesylate, nonaflate, tosylate, sulfonate, and/or phosphate and, when the magnesium atom is inserted via halogen-magnesium exchange, the preferred leaving groups further include sterically hindered sulfoxides such as diaryl sulfoxides.

Preferred organic moieties represented by $R^2$ include each and every preferred organic compound of $R^1$ in Formulae (I) disclosed above. Among those compounds, cyclic compounds, such as aryl, cycloalkyl, and heterocyclic, such as heteroaryl, and unsaturated aliphatic compounds, such as alkenyl, for example allyl(ic), and alkynyl compounds, are preferred. Examples include substituted or unsubstituted benzyl, $C_4$-$C_{24}$ aryl or $C_3$-$C_{24}$ heteroaryl, containing one or more heteroatoms selected from the group consisting of B, O, N, S, Se, P and Si; substituted or unsubstituted linear or branched, $C_2$-$C_{20}$ alkenyl or $C_2$-$C_{20}$ alkynyl; or substituted or unsubstituted $C_3$-$C_{20}$ cycloalkyl.

In addition to the foregoing, the organic moiety may have functional group substituents. Examples of functional group substituents include ethers, amines, azos, triazenes, thioethers, halogens that are less nucleophilic than those involved in the above reactions, sulfones, sulfoxides, olefins, alkynes, allyls, silanes, silylethers, ketones, esters, such as allyl esters, amides, carbonates, carbamates, aldehydes, nitriles, imines, acetates, nitro, nitroso, oxirane, dithiolan, phosphates, phosphonates, sulfates, sulfonates, boronates and hydroxy.

The functional groups preferably do not comprise protonated O, N, or S atoms. Preferred functional group substituents are nitrile, nitro, ester, protected alcohol, protected aldehyde, protected amine and protected amide. The ester group is preferably represented by the formula —$C(O)OR^3$, wherein $R^3$ is an organic moiety, which may be selected from each and every option presented for $R^1$ of Formula (I) above. Protected alcohol, protected aldehyde, protected amine and protected amide are alcohol, aldehyde, amine and amide groups in which each proton bonded to an oxygen atom, carbon atom or nitrogen atom has been replaced with a group that is less reactive than the proton and yet capable of being removed to permit reactions to take place on the respective groups. Protecting groups for those functionalities are well known in the state of the art. Examples of suitable protective groups are disclosed in, T. W. Greene and P. G. M. Wuts, PROTECTIVE GROUPS IN ORGANIC SYNTHESIS, $3^{rd}$ edition (Wiley, 1999), which is incorporated herein by reference for its relevant disclosure. An example is TIPS for protecting alcoholic and phenolic OH groups.

The organomagnesium complex may therefore comprise functional groups, such as the functional groups described above.

The synthesis of the organomagnesium complex is preferably conducted in the presence of LiX, wherein X represents halide selected from Cl, Br, and I. X is preferably Cl. LiX has an accelerating effect on the synthesis of the organomagnesium complex, particularly when the synthesis of the organomagnesium complex is conducted concurrently with synthesis of the organozinc complex in a one pot procedure, which is a preferred mode for synthesizing the organozinc complex. In a particularly preferred method for synthesizing the organozinc complex, LiX is provided in combination with the above-described zinc carboxylate and/or zinc alcoholate to carry out synthesis of the organozinc complex in one step.

The one pot procedure for making organozinc reagents may be, alternatively, be characterized as comprising contacting an organic compound having at least one leaving group with magnesium metal and a zinc coordination complex optionally in the presence of lithium halide, wherein the halide is selected from chloride, bromide and iodide and the zinc coordination complex comprises at least one coordinating compound comprising one or more carboxylate groups and/or alcoholate groups and/or tertiary amine groups. The organic compound having at least one leaving group may be selected from the preceding description, including $R^2Z$ as defined above, including the preferred aspects thereof. The zinc coordination complex may be selected from the preceding description, including the embodiments described above in relation to Formulae (I), (IA) and (IB).

In the one step or one pot procedure, the reactions are preferably carried out in the presence of $ZnX'_2$, wherein X' has the same meaning as X above and is also preferably Cl.

As mentioned above, metalation of an organic compound to obtain the organomagnesium complex may also be conducted via C—H activation by reacting a magnesium amide with an organic compound in the presence of at least one halide and, optionally, in the presence of Li ions. Specific examples of suitable metal amides include magnesium chloride diisopropylamide, tmpMgCl.LiCl, and ClMgHMDS.

The above metal amides are either commercially available or may be prepared by the skilled chemist without undue effort. The metal amide tmpMgCl.LiCl is commercially available from sources such as Sigma Aldrich and Acros Organics. The following table provides examples of citations describing procedures for making the other metal amides. The citations are incorporated herein by reference for their relevant disclosure.

| Metal Amide | Citation |
| --- | --- |
| (HMDS)MgCl | "Silylamino-substituted Grignard compounds", *ANGEWANDTE CHEMIE* (1963), 75, (1), 95 |
| iPr$_2$NMgCl•LiCl | "New mixed Li/Mg/Zn Amides for the Chemoselective Metallation of Arenes and Heteroarenes", *EUR. J. ORG. CHEM.* (2009), 1781-1795 |
| iPr$_2$NMgX | "Magnesium amide bases and amido-Grignards. 1. Ortho magnesiation", *JOURNAL OF THE AMERICAN CHEMICAL SOCIETY* (1989), 111, (20), 8016-18 |

Organozinc Complex

The organozinc complex is an organic compound metalated with Zn. Metalation may by conducted by (1) reacting an organic compound having at least one leaving group with zinc metal to insert a zinc atom via oxidative addition, (2) halogen-zinc exchange, or (3) C—H activation.

Oxidative addition may be conducted in accordance with the following scheme:

$$R^2Z + Zn^0 \rightarrow R^2ZnZ \quad \text{(IIIA)},$$

halogen-zinc exchange may be conducted in accordance with the following scheme:

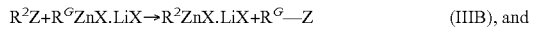

$$R^2Z + R^GZnX \cdot LiX \rightarrow R^2ZnX \cdot LiX + R^G{-}Z \quad \text{(IIIB), and}$$

C—H activation may be conducted in accordance with the following scheme:

$$R^2H + R^HZnX \rightarrow R^2ZnX + R^H{-}H \quad \text{(IIIC)}$$

in which LiX may be present and may be coordinated with ZnX of $R^HZnX$, wherein $R^2$, $R^G$, $R^H$, X, and Z are each defined the same as in Formulae IIA to IIC above.

Reaction Conditions

The syntheses of organomagnesium complex, organozinc complex and organozinc reagent are preferably conducted at a temperature in the range from −30° C. up to, but not including, the decomposition temperature of the reactant having the lowest decomposition temperature. In most cases, the reaction may preferably be conducted at temperatures in the range from 10° C., more preferably from 20° C. up to 50° C., more preferably up to 30° C., such as at ambient (e.g., room) temperature.

The reaction is generally conducted under the exclusion of oxygen, or air, in a nonprotic solvent under an inert atmosphere, such as argon gas, until conversion is complete. Suitable nonprotic solvents include, but are not limited to, cyclic, linear or branched mono- or polyethers such as THF, Me-THF, dibutyl ether, diethylether, tert-butylmethylether, dimethoxyether, and dimethoxyether; thioethers such as dimethyl sulfide and dibutyl sulfide; tertiary amines such as triethylamine, and ethyldiisopropylamine; phosphines; aromatic hydrocarbons, such as benzene, toluene and xylene; heteroaromatic hydrocarbons such as pyridine, N-methyl-2-pyrrolidone (NMP), N-ethyl-2-pyrrolidone (NEP), N-butyl-2-pyrrolidone (NBP); aliphatic hydrocarbons, such as pentane, hexane, or heptane; cycloalkyls such as cyclohexane; dialkyl sulfoxides such as dimethylsulfoxide, amides such as dimethylformamide, N,N-dimethylacetamide and hexamethylphosphortriamide (HMPA); cyclic, linear or branched alkanes in which one or more hydrogen atoms are replaced by halogen atoms, such as dichloromethane, tetrachloromethane, hexachloroethane; urea derivatives such as N,N'-dimethylpropylene urea (DMPU) and N,N,N',N'-tetramethyl urea; acetonitrile; and $CS_2$ either individually or two or more in combination. Cyclic ethers, such as THF and Me-THF, are preferred.

The solvent may be inert solvent or a coordinating solvent vis-à-vis the above-identified reactants and the synthesized product. An example of a coordinating solvent is TMEDA. When the reaction is conducted in the presence of a coordinating solvent, the coordinating solvent may exchange with the carboxylate and/or alcoholate anions coordinated with the zinc ions, so that some or all of the zinc ions are coordinated with the coordinating solvent in addition to, or instead of, the carboxylate and/or alcoholate, respectively.

This reaction is preferably carried out in the substantial absence of protic solvents, such as water. Unless stated otherwise, the solvent has been dried to minimize the presence of protic solvents such as water. The reaction vessel, reactants and solvent are preferably dried or distilled before use to ensure that water is not present during the reaction.

To increase the crystallinity of the resulting organozinc reagent, the ratio of equivalents of the zinc coordinating complex to equivalents of organomagnesium complex or organozinc complex is preferably in the range from 1 to 3, more preferably from 1.1 to 2.8.

The organozinc reagent may be made using an organomagnesium complex as defined above such as by reacting at least one organomagnesium complex with at least one zinc coordination complex as defined above. This reaction may be illustrated by the following preferred scheme:

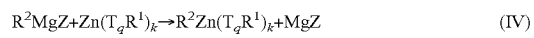

$$R^2MgZ + Zn(T_qR^1)_k \rightarrow R^2Zn(T_qR^1)_k + MgZ \quad \text{(IV)}$$

wherein $R^1$, $R^2$, T, Z, q and k have the same meanings as defined above, including the preferred meanings. When T comprises carboxylate or alcoholate groups, scheme (IV) is preferably conducted in the presence of a lithium halide, such as lithium chloride.

In one embodiment, the syntheses of organomagnesium complex and organozinc reagent are preferably conducted together in a one-pot procedure. By one-pot procedure is meant that the reactions are carried out concurrently, i.e., simultaneously, in the same reaction vessel. Thereby, the organomagnesium complex used as the reactant for making the organozinc reagent is produced in situ during the process for making the organozinc reagent, i.e., the synthesis of the organomagnesium complex is carried out in the presence of the zinc coordinating complex used to make the organozinc reagent. The overall production process is thereby simplified.

Organozinc reagent

The organozinc reagents obtainable via the above-described synthetic processes may be characterized as compositions comprising at least one organozinc compound, at least one coordinating compound, optionally magnesium ions, optionally lithium ions, and optionally halide ions, wherein the halide is selected from chloride, bromide and iodide. When the reaction is conducted in the presence of a coordinating solvent, the coordinating compound may be partly or completely replaced by the coordinating solvent. The organozinc compound preferably comprises aryl, heteroaryl or benzyl optionally having one or more functional group substituents. The functional group substituents, when present, preferably include at least one functional group selected from nitrile, nitro and ester. The compositions preferably comprise $Li^+$, and preferably comprise at least one halide selected from chloride, bromide and iodide.

In a preferred embodiment, the organozinc reagent preferably comprises at least one organozinc cluster represented by $R^2ZnA$, optionally a magnesium complex comprising a moiety represented by $MgAA'$, a lithium salt comprising a moiety represented by $LiA$ and, optionally, a zinc salt comprising a moiety represented by $ZnAA'$, wherein each $A$ and $A'$ is independently selected from Cl, Br, I, and $R^1T_q$, wherein each $R^1$, $R^2$, $T$ and $q$ independently has the same meaning, including the preferred meanings, as defined in Formula (I) above, provided that at least one of $A$ and $A'$ represents $R^1T_q$. In a particularly preferred embodiment, the organozinc reagent preferably comprises an organozinc cluster represented by $R^2ZnA$, a magnesium complex represented by $MgAA'$, a lithium salt represented by $LiA$ and, optionally, a zinc salt represented by $ZnAA'$, wherein each $R^2$, $A$ and $A'$ has the same meaning as defined above, provided that at least one of $A$ and $A'$ represents $R^1T_{q'}$, wherein $R^1T$ and $q$ have the same meaning, including the preferred meanings, as disclosed above for Formula (I).

In particular, $R^1$ and $R^2$ each independently preferably represents a substituted or unsubstituted benzyl, $C_4$-$C_{24}$ aryl or $C_3$-$C_{24}$ heteroaryl, containing one or more heteroatoms selected from the group consisting of B, O, N, S, Se, P and Si; linear or branched, substituted or unsubstituted $C_2$-$C_{20}$ alkyl, $C_2$-$C_{20}$ alkenyl or $C_2$-$C_{20}$ alkynyl; or substituted or unsubstituted $C_3$-$C_{20}$ cycloalkyl. The substituents may be selected from the groups identified above for $R^1$ and $R^2$.

The substituents of $R^2$ may include functional groups such as nitrile, nitro, ester, protected alcohol, protected amine and protected amide. As disclosed above, the ester group is preferably represented by the formula $—C(O)OR^3$, wherein $R^3$ is an organic moiety, which may be selected from each and every option presented for $R^1$ of Formula (I) above.

The molar ratio of Mg to the organozinc complex RZnA in the above organozinc reagent compositions is preferably 1:1.

The molar ratio of Li to RZnA in the above organozinc reagent compositions is preferably at least 1:1 and preferably up to 5:1.

When $ZnAA'$ is present, the molar ratio of $ZnAA'$ to RZnA is preferably not greater than 5:1.

The organozinc reagents may also be made, or modified, by a process comprising complexing an organozinc complex with a coordinating compound in a solvent, such as a solvent described herein, and optionally evaporating the solvent to obtain a solid product. The reaction may, for example, be carried out under ambient conditions.

The organozinc complexes used to make complexes with coordinating compounds may be represented by the chemical formula $R^2{}_nZnA_{2-n}$, wherein $R^2$ and $A$ have the same meaning as defined above and n represents the number 1 or 2. The organozinc complexes may be obtained by the processes described above or may, for example, be obtained by conducting magnesium-halogen exchange reaction as described above for making an organomagnesium complex, transmetalating the product of that reaction with $ZnX'_2$, wherein $X'$ has the same meaning as defined above (such as Cl), and, optionally, precipitating the magnesium salts, such as by contacting the reaction mixture with dioxane, prior to reacting the product with a coordinating compound. The coordinating compound is preferably a Lewis base which is preferably a stronger Lewis base than $R^2$, and $A$ when present.

This reaction may be illustrated by the following schemes:

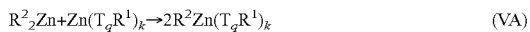

(VA)

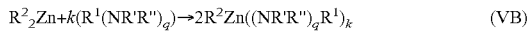

(VB)

wherein $R^1$, $R^2$, $T$, $R'$, $R''$ and $q$ have the same meanings as defined above, including the preferred meanings. Scheme (VA) is preferably conducted in the presence of a lithium halide, such as lithium chloride.

$R^2{}_2Zn$, above, may be made by reacting at least one organomagnesium compound $R^2MgZ$ with at least one zinc compound having the formula $ZnZ_2$, wherein $R^2$ and $Z$ have the same meaning as defined above, as illustrated by the following preferred scheme (VC):

(VC).

wherein $R^2$ and $Z$ have the same meanings as defined above, including the preferred meanings.

The organozinc reagents may also be made by a process comprising reacting (A) at least one organozinc complex with (B) at least one coordinating compound comprising one or more carboxylate groups and/or alcoholate groups and/or tertiary amine groups in combination with zinc ions and/or lithium ions, optionally in combination with halide ions, wherein the halide ions are selected from chloride, bromide and iodide and the organozinc complex comprises an aryl group, a heteroaryl group or a benzyl group when the coordinating compound is a chelating polyamine. Preferred organozinc complexes and preferred coordinating compounds may be selected from the preferred organozinc complexes and preferred coordinating compounds defined above.

In particular, the organozinc reagent may be made by reacting at least one organozinc complex with at least one lithium coordinating complex. This reaction may be illustrated by the following preferred scheme (VI):

(VI)

wherein $R^1$, $R^2$, $T$ and $Z$ have the same meaning as defined above, including the preferred meanings. In this scheme, Z is preferably X, as defined above, and T is preferably a carboxylate, such as pivalate, and/or an alcoholate, such as tert-butoxylate.

The organozinc reagents may also be made, or modified, by a process comprising complexing an organozinc complex with a coordinating compound in a solvent, such as a solvent described herein, and optionally evaporating the solvent to obtain a solid product. The reaction may, for example, be carried out under ambient conditions.

The latter processes which start from an organozinc complex may be carried out in the absence, or substantial absence, of Mg and/or organomagnesium complex. Such processes are preferred for making organozinc reagents having sensitive functional groups, such as nitriles, nitro, esters, ketones, protected alcohols, protected amines, protected amides and aldehydes, from organozinc complexes comprising one or more of the same. The inventors have found that the preservation of sensitive functional groups in the organozinc reagent may be facilitated by conducting the reaction in the absence, or substantial absence, of Mg and/or organomagnesium complexes. The organozinc reagents produced by those processes may be represented by the chemical formula $R^2{}_nZnA_{2-n}Q$, wherein $R^2$, A, and n have the same meaning as defined above for $R^2{}_nZnA_{2-n}$ and each Q represents a coordinating compound molecule. The product may optionally be isolated from solvent via evaporation of the solvent, such as by applying gentle heat and vacuum. See footnotes "d" and "f" of Table 2, for example.

An important advantage of the organozinc reagents according to this invention is that they can be solidified by removing the solvent, such as by evaporating the solvent from the composition. Removal of the solvent reduces the cost and hazard of transporting and storing industrial quantities the organozinc reagent and reduces variability in the concentration of active component due to solvent evaporation. When granulated, the solid form can easily be introduced into a reaction vessel in an accurately measured amount, thereby overcoming handling problems associated with liquids, particularly the viscous liquids formed by the state of the art organozinc reagent upon solvent evaporation. The solid composition, including its method of preparation, is therefore a significant improvement over the state of the art.

End use applications

The organozinc reagents obtainable according to this invention are useful for conducting cross-coupling reactions with electrophiles. In a preferred embodiment, the electrophile is selected from organic compounds having one or more of the (nucleophilic) leaving groups identified above. In a preferred embodiment, the electrophile is selected from halide-, triflate-, mesylate-, nonaflate-, tosylate-, sulfonate- and/or phosphate-substituted organic compounds, wherein the halide may be selected from Cl, Br and I. The electrophile may be reacted with the above-described organozinc reagent in the presence of a cross-coupling catalyst to couple the electrophile residue with the organo portion of the organozinc reagent.

The electrophile may optionally have one or more functional groups, including functional groups previously considered too sensitive (i.e., too reactive) with the organometallic complex for use in such coupling reactions due to side reactions between the metal and the functional group. Examples of such functional groups include nitriles, including enolizable benzylic nitriles, nitro, esters, ketones, protected alcohols, protected amines, protected amides, and aldehydes. The ability to conduct coupling in the presence of aldehyde groups on the electrophile is an unusual and unexpected advantage of this invention.

The catalyst is preferably of the type used in Negishi cross-coupling reactions. Appropriate catalysts are well-known. A preferred catalyst is PEPPSI™-iPr.

The coupling reaction is preferably conducted in a solvent disclosed above as suitable or preferred for use in synthesis of the organozinc reagent and furthermore may be performed in other solvents, such as esters of carboxylic acid or carboxylic acid anhydrides. In contrast to solvents used in the state of the art, the solvents may be used without distillation or predrying.

Preferred ester solvents include aliphatic hydrocarbon esters of carboxylic acids, preferably having at least 1, more preferably at least 2, preferably up to 12, more preferably up to 8, and even more preferably up to 6, carbon atoms in the ester group, preferably having up to 12, more preferably up to 8 and even more preferably up to 4 carbon atoms in the carboxylic acid, and preferably up to 4, more preferably up to 2, and even more preferably 1, carboxylic acid group. In a preferred embodiment, the carboxylic acid ester has at least 4 carbon atoms, more preferably at least 5 carbon atoms, up to 10 carbon atoms, more preferably up to 8 carbon atoms. An example of a preferred solvent is ethyl acetate. The inventors have found that use of ester solvents, particularly the preferred ester solvents, can improve product yield.

The temperature range for coupling is also preferably in a temperature range disclosed above as suitable or preferred for synthesis of the organozinc reagent.

Information regarding appropriate catalysts and reaction conditions may be found in *Metal Catalyzed Cross Coupling Reactions*, $2^{nd}$ edition (A. de Meijere, F. Diederich, eds.), Wiley-VCH, Weinheim, 2005, A. Krasovskiy, V. Malakhov, A. Gavryushin, P. Knochel, *Angew. Chem. Int. Ed.* 2006, 45, 6040, N. Boudet, S. Sase, P. Sinha, C.-Y. Liu, A. Krasovskiy, P. Knochel, *J. Am. Chem. Soc.* 2007, 129, 12358, and A. Metzger, M. Schade, P. Knochel, *Org. Lett.* 2008, 10, 1108.

The organozinc reagents obtainable according to this invention may also be reacted with the aldehyde of aldehyde-substituted organic compounds to synthesize organic compounds via an aldehyde addition reaction. When the organozinc reagent is applied in this manner, either the aldehyde-substituted organic compound does not have an electrophilic leaving group such as the electrophiles described above or the reaction is conducted in the absence of the above-described coupling catalyst.

This latter reaction may be conducted in solvents and under reaction conditions (e.g., temperature ranges and oxygen-free atmosphere) that are the same as, or similar to, those already disclosed above for synthesizing the organozinc reagent and/or for conducting cross-coupling reactions.

When the aldehyde-substituted organic compound has an nucleophilic leaving group, such as Cl, Br, I, triflate, mesylate, nonaflate, and/or phosphate, the reaction can be "tuned" via the presence or absence of coupling catalyst to conduct substitution at either the leaving group or the aldehyde. In the presence of the coupling catalyst, the organo portion of the organozinc reagent replaces the leaving groups. In the absence of coupling catalyst, the organo portion of the organozinc reagent is added to the aldehyde-substituted organic compound via addition reaction at the aldehyde.

The invention is now illustrated by way of the following examples.

EXAMPLES

Preparation of Zinc Pivalate.2LiCl (2a)

Pivalic acid (20.4 g, 22.6 mL, 200 mmol) is placed in a dry and argon-flushed 500 mL Schlenk-flask equipped with a magnetic stirring bar and a septum, and the pivalic acid is dissolved in dry THF (100 mL). The solution is cooled to 0° C. and methyllithium (135 mL, 1.63 M in diethyl ether, 220 mmol) is added dropwise. After the evolution of methane gas has stopped, $ZnCl_2$ in THF (100 mL, 1.0 M, 100 mmol) is added and the mixture is stirred for 2 h at 25° C. The solvent is removed in vacuo and zinc pivalate.2LiCl (2a) is obtained as a colourless solid in quantitative yield.

Preparation of Zinc Tert-Butylate.2LiCl (2b)

Tert-butanol (1.85 g, 2.39 mL, 25.0 mmol) is placed in a dry and argon-flushed 250 mL Schlenk-flask equipped with a magnetic stirring bar and a septum, and tert-butanol is dissolved in dry THF (25.0 mL). The solution is cooled to 0° C. and methyllithium (15.0 mL, 1.83 M in diethyl ether, 27.5 mmol) is added dropwise. After the evolution of methane gas has stopped, $ZnCl_2$ in THF (12.5 mL, 1.00 M, 12.5 mmol) is added and the mixture is stirred for 2 h at 25° C. The solvent is removed in vacuo and zinc tert-butylate 2LiCl (2b) is obtained as a colourless solid in quantitative yield.

Example 1

Preparation of 3-(trifluoromethyl)phenylzinc pivalate (1c)

Zinc pivalate.2LiCl (2a prepared above; 2.64 g, 7.50 mmol) is placed in a 25 mL Schlenk-flask, dried for 5 min at 400° C. (heat gun) in high vacuum and then dissolved in dry THF (10.0 mL). 1-Bromo-3-(trifluoromethyl)benzene (3d; 1.13 g, 5.00 mmol) and magnesium-turnings (304 mg, 12.5 mmol) are added and the mixture was stirred for 2 h at 25° C. The solution is cannulated to a dry and argon-flushed 50 mL Schlenk-tube via syringe filter and the solvent is removed in vacuo. 3-(Trifluoromethyl)phenylzinc pivalate (1d) is obtained as a grey solid (3.72 g).

The content of active zinc species is determined by titration of 300 mg of the reagent with a stock solution of iodine (1.0 M in THF). A concentration of 882 mg/mmol was determined which corresponds to a yield of 84%.

The 3-(trifluormethyl)phenylzinc pivalate (1d) product can be stored under inert gas atmosphere at ambient temperature for one week without any loss of activity (entry 1, Table 1 below). After 5 minutes of storage in air, 95% of active zinc species could be determined by titration (Table 1, entry 2). After 15 minutes, the activity is reduced to 58% (Table 1, entry 3) and after 30 and 45 minutes, activities of 43% and 40% are obtained (Table 1, entries 4-5). After storage on air for 60 minutes, active zinc species cannot be detected (Table 1, entry 6).

TABLE 1

Stability of 3-(Trifluormethyl)phenylzincpivalate (1d)

| Entry | Treatment | Active Zinc Complex 1d (%)[a] |
|---|---|---|
| 1 | storage under inert gas (7 d) | 100 |
| 2 | storage on air (5 min) | 95 |
| 3 | storage on air (15 min) | 58 |
| 4 | storage on air (30 min) | 43 |
| 5 | storage on air (45 min) | 40 |
| 6 | storage on air (60 min) | 0 |

[a]Determined by titration with a stock solution of iodine (1.0 M in THF)

Example 2

Preparation of (4-methoxyphenyl)zinc tert-butylate (1r)

tert-butylate 2LiCl (2b prepared above; 2.22 g, 7.50 mmol) is placed in a 25 mL Schlenk-flask, dried for 5 min at 400° C. (heat gun) in high vacuum and then dissolved in dry THF (10.0 mL). 4-bromoanisol (3a; 935 mg, 5.00 mmol) and magnesium-turnings (304 mg, 12.5 mmol) are added and the mixture is stirred for 2 h at 25° C. The solution is cannulated to a dry and argon-flushed 50 mL Schlenk-tube via syringe filter and the solvent is removed in vacuo. (4-methoxyphenyl) zinc tert-butylate (1r) is obtained as a grey solid (3.33 g).

The content of active zinc species is determined by titration of 293 mg of the reagent with a stock solution of iodine (1.0 M in THF). A concentration of 977 mg/mmol was determined which corresponds to a yield of 68%.

Example 3

Additional Organozinc Complex Examples

Starting from 4-bromoanisole (3a) and the TIPS-protected 4-bromophenol 3b, the corresponding organozinc reagents 1a and 1b are prepared analogous to Example 1 in presence of 1.0 equivalent of the zinc pivalate.2LiCl (2a) prepared above in 78-84% (Table 2, entries 1-2).

The magnesium insertion in presence of 1.5 equiv of $Zn(OPiv)_2 \cdot 2LiCl$ (2a) into 1-bromo-4-fluorobenzene (3c) and 1-bromo-3-(trifluoromethyl)benzene (3d) leads to the organozinc species 1c (Example 1 above) and id in 70-84% yield (Table 2, entries 3-4).

Furthermore p-trimethylsilylphenylzinc pivalate (1e) is obtained in presence of 1.5 equiv of $Zn(OPiv)_2 \cdot 2LiCl$ (2a) in 81% yield (entry 5).

Applying this methodology, sensitive functionalities like a nitrile- or an ester group can be tolerated. Using ethyl 4-bromobenzoate (3f) and 4-bromobenzonitrile (3h), the para-substituted organozincs 1f and 1g are accessible in presence of 1.5 equivalent of the zinc pivalate salt 2a in 59-64% (entries 6-7) by the one-pot oxidative addition protocol.

A modified synthetic procedure based on a halogen-magnesium exchange with iPrMgCl.LiCl and subsequent transmetalation with $Zn(OPiv)_2 \cdot 2LiCl$ (2a; 1.5 equiv) improved the yields to 71-89%. The precipitation and separation of the magnesium salts before the evaporation of the solvent leads to a comparable yield of 71% in the case of the zinc coordination complex reagent 1f and to a lower yield (59%) for coordination complex reagent 1g (entries 6-7).

The heteroaromatic bromides 3i and 3j gives access to (pyridine-3-yl)zinc pivalate (1h) and (2,4-dimethoxypyrimidine-5-yl)zinc pivalate (1i) in 65-70% yield (entries 8 and 9) in the presence of 1.5 equiv of $Zn(OPiv)_2 \cdot 2LiCl$ (2a).

Moreover, it is possible to prepare (3,5-dimethylisoxazol-4-yl)zinc pivalate (1j) and (3-methyl-1-phenyl-1H-pyrazol-5-yl)zinc pivalate (1k) in 50-71% yield in the presence of 1.5 equivalent of $Zn(OPiv)_2 \cdot 2LiCl$ (2a) (entries 10-11).

Benzylic zinc reagents can also be obtained as solid materials starting from the corresponding benzylic chlorides. Thus, 4-fluorobenzylzinc pivalate (1l; 1.5 equiv. of $Zn(OPiv)_2 \cdot 2LiCl$ (2a)) and 2-chlorobenzylzinc pivalate (1m; 2.0 equiv of $Zn(OPiv)_2 \cdot 2LiCl$ (2a)) are synthesized in 68-80% yield (entries 12-13).

The meta-trifluoromethyl-, meta-ethylester- and meta-methoxy substituted benzylzinc pivalates 1n, 1o and 1p are prepared in 67-68% yield in the presence of 1.5 equiv. of $Zn(OPiv)_2 \cdot 2LiCl$ (2a) (entries 14-16).

Finally the heterobenzylic ((6-chloropyridin-3-yl)methyl) zinc pivalate (1q) is obtained in 59% yield in the presence of 1.5 equiv of $Zn(OPiv)_2 \cdot 2LiCl$ (2a) (entry 17).

Furthermore, $Zn(O-tert-Bu)_2 \cdot 2LiCl$ may also be used as transmetalation agent. Starting from 4-bromoanisole (3a) the corresponding organozinc coordination complex reagent 1r is prepared analogous to Example 3 in the presence of 1.5 equivalents of zinc tert-butoxylate.2LiCl (2b) in 68% yield (Table 2, entry 18).

TABLE 2

Preparation of solid organozinc coordination complex reagents by Mg-insertion in the presence of Zn(OPiv)$_2$·2LiCl (2a) or Zn(O$^t$Bu)$_2$·2LiCl (2b).

| Entry No. | Substrate | Equivalents of Zn(OR)$_2$·2LiCl | Organozinc Complex[a] | Yield (%) |
|---|---|---|---|---|
| 1 | 4-MeO-C$_6$H$_4$-Br (3a) | 1.0 equiv. 2a; OR = pivalate | 4-MeO-C$_6$H$_4$-ZnOPiv (1a) | 78[b] |
| 2 | 4-TIPSO-C$_6$H$_4$-Br (3b) | 1.0 equiv. 2a; OR = pivalate | 4-TIPSO-C$_6$H$_4$-ZnOPiv (1b) | 84[b] |
| 3 | 4-F-C$_6$H$_4$-Br (3c) | 1.5 equiv. 2a; OR = pivalate | 4-F-C$_6$H$_4$-ZnOPiv (1c) | 70[b] |
| 4 | 3-CF$_3$-C$_6$H$_4$-Br (3d) | 1.5 equiv. 2a; OR = pivalate | 3-CF$_3$-C$_6$H$_4$-ZnOPiv (1d) | 84[b] |
| 5 | 4-TMS-C$_6$H$_4$-Br (3e) | 1.5 equiv. 2a; OR = pivalate | 4-TMS-C$_6$H$_4$-ZnOPiv (1e) | 81[b] |
| 6 | 4-EtO$_2$C-C$_6$H$_4$-X; 3f (X = Br), 3g (X = I) | 1.5 equiv. 2a; OR = pivalate | 4-EtO$_2$C-C$_6$H$_4$-ZnOPiv (1f) | 59 (X = Br)[b]; 72 (X = I)[c]; 71 (X = I)[d] |
| 7 | 4-NC-C$_6$H$_4$-Br (3h) | 1.5 equiv. 2a; OR = pivalate | 4-NC-C$_6$H$_4$-ZnOPiv (1g) | 64[b]; 89[e]; 59[f] |
| 8 | 3-bromopyridine (3i) | 1.5 equiv. 2a; OR = pivalate | 3-pyridyl-ZnOPiv (1h) | 70[b] |
| 9 | 4-OMe, 2-OMe, 5-Br-pyrimidine (3j) | 1.5 equiv. 2a; OR = pivalate | 4-OMe, 2-OMe, 5-ZnOPiv-pyrimidine (1i) | 65[b] |

TABLE 2-continued

Preparation of solid organozinc coordination complex reagents by Mg-insertion in the presence of Zn(OPiv)$_2$•2LiCl (2a) or Zn(O$^t$Bu)$_2$•2LiCl (2b).

| Entry No. | Substrate | Equivalents of Zn(OR)$_2$•2LiCl | Organozinc Complex[a] | Yield (%) |
|---|---|---|---|---|
| 10 | 3k (3,5-dimethyl-4-bromoisoxazole) | 1.5 equiv. 2a OR = pivalate | 1j (3,5-dimethyl-4-ZnOPiv-isoxazole) | 71[b] |
| 11 | 3l (1-Ph-3-Me-5-Cl-pyrazole) | 1.5 equiv. 2a OR = pivalate | 1k (1-Ph-3-Me-5-ZnOPiv-pyrazole) | 50[b] |
| 12 | 3m (4-fluorobenzyl chloride) | 1.5 equiv. 2a OR = pivalate | 1l (4-fluorobenzyl ZnOPiv) | 80[b] |
| 13 | 3n (2-chlorobenzyl chloride) | 2.0 equiv. 2a OR = pivalate | 1m (2-chlorobenzyl ZnOPiv) | 68[b] |
| 14 | 3o (3-CF$_3$-benzyl chloride) | 1.5 equiv. 2a OR = pivalate | 1n (3-CF$_3$-benzyl ZnOPiv) | 67[b] |
| 15 | 3p (3-CO$_2$Et-benzyl chloride) | 1.5 equiv. 2a OR = pivalate | 1o (3-CO$_2$Et-benzyl ZnOPiv) | 68[b] |
| 16 | 3q (3-OMe-benzyl chloride) | 1.5 equiv. 2a OR = pivalate | 1p (3-OMe-benzyl ZnOPiv) | 67[b] |
| 17 | 3r (2-chloro-5-(chloromethyl)pyridine) | 1.5 equiv. 2a OR = pivalate | 1q (2-chloro-5-(ZnOPiv-methyl)pyridine) | 59[b] |

TABLE 2-continued

Preparation of solid organozinc coordination complex reagents by Mg-insertion in the presence of Zn(OPiv)$_2$•2LiCl (2a) or Zn(O$^t$Bu)$_2$•2LiCl (2b).

| Entry No. | Substrate | Equivalents of Zn(OR)$_2$•2LiCl | Organozinc Complex[a] | Yield (%) |
|---|---|---|---|---|
| 18 | 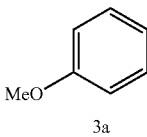 3a | 1.5 equiv. 2b OR = tert-butylate | 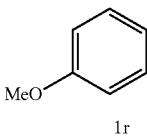 1r | 68[g] |

[a]Complexed zinc and magnesium salts as well as LiCl are omitted for the sake of clarity.
[b]Prepared from the corresponding aryl halide by magnesium insertion in the presence of Zn(OPiv)$_2$•2LiCl.
[c]Prepared from the corresponding aryl halide by exchange with iPrMgCl•LiCl (1.1 equiv, THF, −30° C., 30 min) and subsequent transmetalation with Zn(OPiv)$_2$•2LiCl (1.5 equiv).
[d]Prepared from the corresponding aryl halide by exchange with iPrMgCl•LiCl (1.1 equiv, THF, −30° C., 30 min) followed by transmetallation with ZnCl$_2$ (0.5 equiv) subsequent precipitation of the magnesium salts with dioxane (10% v/v) and addition of Zn(OPiv)$_2$•2LiCl (0.5 equiv).
[e]Prepared from the corresponding aryl halide by exchange with iPrMgCl•LiCl (1.05 equiv, THF, 0° C., 2 h) and subsequent transmetalation with Zn(OPiv)$_2$•2LiCl (1.5 equiv).
[f]Prepared from the corresponding aryl halide by exchange with iPrMgCl•LiCl (1.05 equiv, THF, 0° C., 2 h) followed by transmetallation with ZnCl$_2$ (0.5 equiv) subsequent precipitation of the magnesium salts with dioxane (10% v/v) and addition of Zn(OPiv)$_2$•2LiCl (0.5 equiv).
[g]Prepared from the corresponding aryl halide by magnesium insertion in the presence of Zn(O$^t$Butyl)$_2$•2LiCl.

Example 4

Preparation of bis-[4-ethoxycarbonyl]phenyl]zinc-TMEDA reagent (1s)

In this example, an iodine-magnesium exchange reaction on ethyl-4-iodobenzoate (3g) is performed using iPrMgCl-.LiCl. After transmetallation with 0.5 equiv. of ZnCl$_2$ and precipitation of the formed magnesium salts with dioxane the corresponding bisarylzinc reagent is formed. After addition of 0.5 equiv. of TMEDA and evaporation of the solvent the solid organozinc-TMEDA-reagent is obtained in 70% yield (Scheme VII).

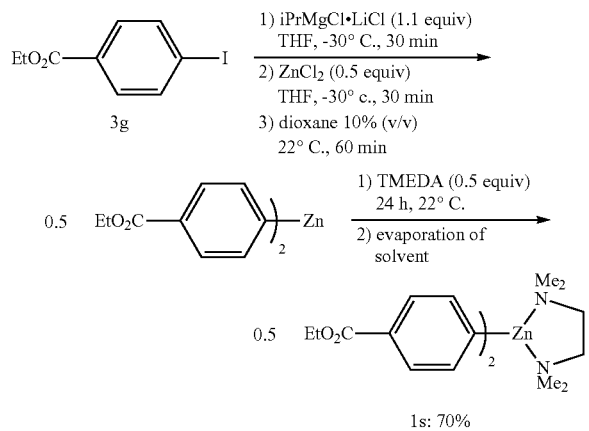

Scheme VII: Preparation of the solid organozinc-TMEDA-complex 1s.

Bis-[4-ethoxycarbonyl]phenyl]zinc (10.0 mL, 0.34 M in THF, 3.40 mmol) is added to TMEDA (0.51 mL, 3.40 mmol) in THF (5 mL). The reaction mixture is stirred for 24 h at 21° C. The solvent is removed in vacuo. Bis-[4-ethoxycarbonyl] phenyl]zinc-TMEDA reagent (1s) is obtained as a grey solid (1.92 g).

The content of active zinc species is determined by titration of 121 mg of the reagent with a stock solution of iodine (1.0 M in THF). A concentration of 807 mg/mmol was determined which corresponds to a yield of 70%.

Example 4A

Preparation of 2-cyanoethylzinc pivalate reagent (1t)

Pivalic acid (5.11 g, 5.74 mL, 50.0 mmol) was placed in a dry and argon-flushed 250 mL Schlenk-flask, equipped with a magnetic stirring bar and a septum, and dissolved in dry THF (30 mL). The solution was cooled to 0° C. and methyllithium (32.4 mL, 1.70 M in diethyl ether, 55.0 mmol) was added dropwise over a period of 45 min. The solvent was removed in vacuo and LiOPiv was obtained as a slightly yellow solid in quantitative yield.

Zinc powder (490 mg, 7.5 mmol) and LiCl (318 mg, 7.5 mmol) were placed in a Schlenk-flask, equipped with a magnetic stirrer and a septum, dried for 5 min at 400° C. (heat gun) in high vacuum and then dissolved in 7.0 mL of dry THF. 4 drops of 1,2-dibromoethane were added and the mixture was heated to boiling for the activation of the zinc dust. After cooling to 22° C. 3-iodopropionitrile (905 mg, 5.0 mmol) was added dropwise and the mixture was stirred for 2 h at 22° C. The stirring of the reaction mixture was stopped and the excess zinc dust was sedimented. The supernatant solution was transferred to another Schlenk-flask containing a solution of lithium pivalate (811 mg, 1.50 mmol) prepared as described above in 5.0 mL of dry THF. The mixture was stirred for 15 min at 22° C. and then the solvent was removed in vacuo. (2-cyanoethyl)zinc pivalate was obtained as a yellow solid (2.94 g). The content of active zinc species was determined by titration of 398 mg of the reagent with a stock solution of iodine (1.0 M in THF). A concentration of 1020 mg/mmol was determined which corresponds to a yield of 58%.

Example 4B

Preparation of (2-((tert-butoxycarbonyl)oxy)-6-(ethoxycarbonyl)phenyl)zinc pivalate (1u)

In a dry and argon-flushed Schlenk-flask, equipped with a magnetic stirring bar and a septum, ethyl 3-((tert-butoxycarbonyl)oxy)benzoate (266 mg, 1.00 mmol) was dissolved in dry THF (3.0 mL). TMPMgCl.LiCl (1.00 mL, 1.2 M in THF, 1.20 mmol) was added dropwise and the mixture was stirred for 4 h at 0° C. A solution of Zn(OPiv)$_2$.2 LiCl (529 mg, 1.50 mmol) in 1.5 mL of dry THF was added and the mixture was slowly warmed to 22° C. The solvent was removed in vacuo and (2-((tert-butoxycarbonyl)oxy)-6-(ethoxycarbonyl)phenyl)zinc pivalate was obtained as a orange solid.

Example 5

Preparation of 6-[3-(trifluoromethyl)phenyl]pyridine-2-carbonitrile (4b)

In this example, the reactivity of the solid zinc reagents towards palladium-catalyzed Negishi-cross-coupling reactions is demonstrated.

In a dry and argon-flushed 25 mL Schlenk-flask, equipped with a magnetic stirring bar and a septum, 3-(trifluoromethyl)phenylzinc pivalate (1d prepared above; 780 mg, 882 mg/mmol, 0.88 mmol) is dissolved in dry THF (1.8 mL). 6-Bromopyridine-2-carbonitrile (5e; 135 mg, 0.74 mmol) and PEPPSI-iPr (14 mg, 0.02 mmol) are added and the mixture is stirred for 2 h at 25° C. Saturated aqueous NH$_4$Cl (10 mL) is added and the aqueous layer is extracted with diethyl ether (3×15 mL). The combined organic layers are dried over sodium sulfate and the solvent is removed in vacuo.

Purification by flash chromatography (silica gel, pentane/Et$_2$O=1:1) affords 6-[3-(trifluoromethyl)phenyl]pyridine-2-carbonitrile (6f; 144 mg, 0.58 mmol, 78%) as a colourless solid.

Example 6

Additional Negishi Cross-coupling Examples

In presence of 2 mol % of the catalyst PEPPSI, cross-coupling reactions can be performed under mild conditions with various electrophiles in good to excellent yields (Table 3).

Thus, 4-methoxyphenylzinc pivalate (1a) coupled with 4-bromobenzonitrile (3h) at 25° C. in 2 h and furnishes the biphenyl 6a in 86% yield (entry 1).

(4-((triisopropylsilyl)oxy)phenyl)zinc pivalate (1b) reacted in 2h at 50 C with 4-bromo-3-fluorobenzonitrile (5a) and leads to carbonitrile 6b in 89% (entry 2).

The 4-fluorozinc pivalate 1c can be coupled smoothly at room temperature with different halocarbonitriles in good yields (entries 3-4). Thus, the coupling with 4-chlorobenzonitrile (5b) furnishes the coupling product 6c in 80% yield.

Remarkably, the unprotected amine function in 4-amino-3-bromobenzonitrile (5c) is well tolerated in the one-pot coupling procedure and the biphenyl 6d was isolated in 79% yield.

3-(4-fluorophenyl)quinoline (6e) is obtained in quantitative yield from the coupling with 3-bromoquinoline (5d; entry 5).

3-(trifluormethyl)phenylzinc pivalate (1d) also reacted at ambient temperature with 6-bromopyridine-2-carbonitrile (5e) and ethyl 4-bromobenzoate (3f) leading to the cross coupling products 6f and 6g in 78-98% yield (entries 6-7).

p-trimethylsilylphenylzinc pivalate (1e) shows a clean reaction with 4-bromoacetophenone (5f) to 1-(4'-(trimethylsilyl)-[1,1'-biphenyl]-4-yl)ethanone (6h) in 83% yield. No side products due to potential enolate formation or addition to the keto-functionality is observed (entry 8).

The ester-substituted aromatic zinc reagent 1f can be coupled smoothly with the heteroaromatic chloride 5g and the unprotected amide 5h at 22° C. in 84-87% yield (entries 9-10).

(4-cyanophenyl)zinc pivalate (1g) reacts well with different aromatic and heteroaromatic bromides and the corresponding cross-coupling products are obtained in 56-88% yield (entries 11-13).

The reaction of (pyridine-3-yl)zincpivalate 1h with 2-chloronicotinonitrile (5g) lead to the 2,3'-bipyridine 6n at 50° C. in 91% yield (entry 14).

The heteroaryl zinc reagent 1i reacts with 4-bromophenylpivalate (5k) and 4-bromonitrobenzene (5l) to form the arylated pyrimidines 6o and 6p in 71-80% yield (entries 15-16).

(3,5-dimethylisoxazol-4-yl)zinc pivalate (1j) and (3-methyl-1-phenyl-1H-pyrazol-5-yl)zinc pivalate (1k) both couple with 4-bromo-3-fluorobenzonitrile (5a) at 50° C. in quantitative yields (entries 17-18).

(4-Fluorobenzyl)zinc pivalate (1l) shows a clean coupling reaction with 3-bromo-4-methoxybenzaldehyde (5m) and afford 3-(4-fluorobenzyl)-4-methoxybenzaldehyde (6s) in 82% yield without observance of any addition products towards the aldehyde functionality (entry 19).

Furthermore, the coupling with 2-(4-bromophenyl)acetonitrile (5n) affords 2-(4-(4-fluorobenzyl)phenyl)acetonitrile (6t) in 78% yield (entry 20).

(2-Chlorobenzyl)zinc pivalate (1m) is coupled to the benzonitrile derivative 6u in 70% yield (entry 21).

(3-(Trifluoromethyl)benzyl)zinc pivalate (1n) reacts smoothly with 3-bromo-1-(phenylsulfonyl)-1H-indole (5o) and the benzocain derivative 5j, bearing a unprotected amine function, in good yields (66-86%; entries 22-23).

(3-(Ethoxycarbonyl)benzyl)zinc pivalate (1o) is reacted with the bromoindole 5o and 5-bromo-2,4-dimethoxypyrimidine (3j) in 55-78% yield (entries 24-25).

In a dry and argon-flushed Schlenk-flask, equipped with a magnetic stirring bar and a septum, (2-cyanoethyl)zinc pivalate (1t) (2.35 g, 2150 mg/mmol, 1.09 mmol) was dissolved in a mixture of THF (3.0 mL) and NMP (1.0 mL). 4-Bromobenzonitrile (168 mg, 0.92 mmol) was added followed by PEPPSI-iPr (14 mg, 0.02 mmol) and the mixture was stirred for 12 h at 50° C. Then sat. aq. NH$_4$Cl (10 mL) was added and the aqueous layer was extracted with EtOAc (3×20 mL). The combined organic phases were dried (Na$_2$SO$_4$). Evaporation of the solvents in vacuo and purification by flash chromatography (silica gel, ihexane/Et$_2$O=3:1) afforded 4-(2-cyanoethyl)benzonitrile (entry 26) (113 mg, 80%) as a pale yellow oil.

Furthermore, (2-((Tert-butoxycarbonyl)oxy)-6-(ethoxycarbonyl)phenyl)zinc pivalate (1u) was dissolved in 2.0 mL of dry THF and 4-bromobenzonitrile (164 mg, 0.91 mmol) and Pd(OAc)$_2$ (4 mg, 0.02 mmol) as well as S-Phos (16 mg, 0.04 mmol) were added and the mixture was stirred at 22° C. for 12 h. Then sat. aq. NH$_4$Cl (10 mL) was added and the aqueous layer was extracted with EtOAc (3×20 mL). The combined organic phases were dried (Na$_2$SO$_4$). Evaporation of the solvents in vacuo and purification by flash chromatography (silica gel, ihexane/EtOAc=12:1 to 6:1) afforded the benzonitrile ethyl 4'-cyano-6-((tert-butoxycarbonyl)oxy)-[1,1'-biphenyl]-2-carboxylate (262 mg, 79%) as a pale yellow oil (entry 27).

In addition, cross-coupling of the organozinc pivalates can also be performed in ester solvents such as ethyl acetate. Thus, the (4-(ethoxycarbonyl)phenyl)zinc pivalate (1f) was reacted with the chloro-pyridine 5g and the bromo-indole 5o in technical grade ethyl acetate as purchased from Sigma-Aldrich having a label purity of 99% without prior drying or distillation to make the corresponding cross-coupling products 6ab and 6ac at 25° C. in 2 h in 96-99% yield (entries 28-29).

Similar results were obtained when reacting the (4-(ethoxycarbonyl)phenyl)zinc pivalate (1f) with ethyl 4-bromobenzoate (3f) in technical grade ethyl acetate to make the corresponding cross-coupling product 6ad at 25° C. in 2 h in 94% yield (entry 30).

TABLE 3

Negishi-cross-coupling reactions of solid organozinc complexes with various electrophiles

| Entry No. | Organozinc Complex[a] | Electrophile | Product | Time, Temperature, Solvent | Yield [%][b] |
|---|---|---|---|---|---|
| 1 | 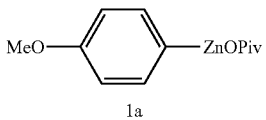 1a | 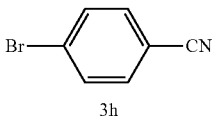 3h | 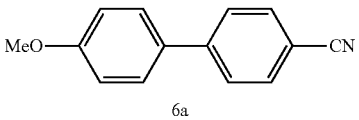 6a | 2 h, 25° C., THF | 86 |
| 2 | 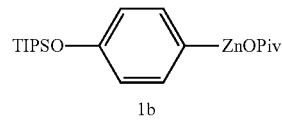 1b | 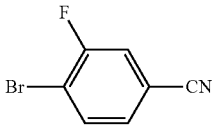 5a | 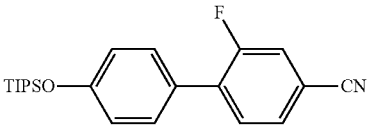 6b | 2 h, 50° C., THF | 89 |
| 3 | 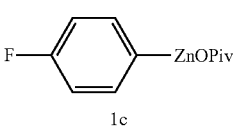 1c | 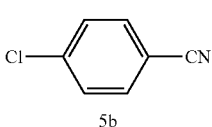 5b | 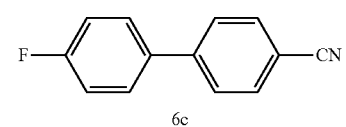 6c | 2 h, 25° C., THF | 80 |
| 4 | 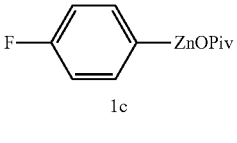 1c | 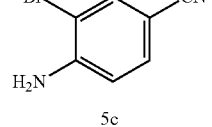 5c | 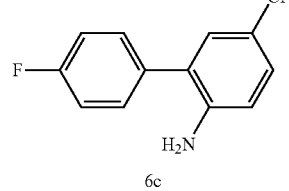 6c | 2 h, 25° C., THF | 79 |
| 5 | 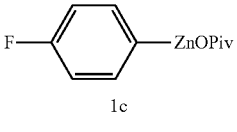 1c | 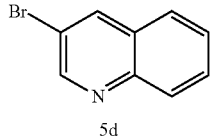 [SMILES: Brc1cnc2ccccc2c1] 5d | 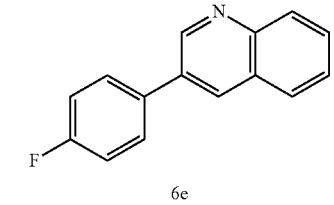 [SMILES: Fc1ccc(-c2cnc3ccccc3c2)cc1] 6e | 2 h, 25° C., THF | 99 |
| 6 | 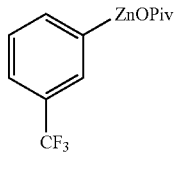 1d | 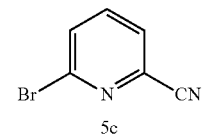 5e | 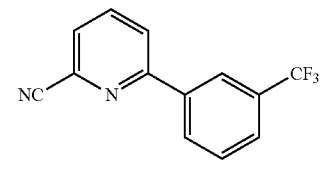 6f | 2 h, 25° C., THF | 78 |
| 7 | 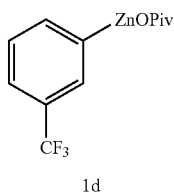 1d | 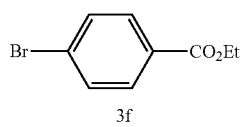 [SMILES: CCOC(=O)c1ccc(Br)cc1] 3f | 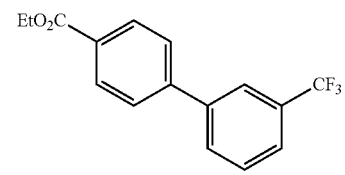 6g | 2 h, 25° C., THF | 98 |

TABLE 3-continued
Negishi-cross-coupling reactions of solid organozinc complexes with various electrophiles
| Entry No. | Organozinc Complex[a] | Electrophile | Product | Time, Temperature, Solvent | Yield [%][b] |
|---|---|---|---|---|---|
| 8 | 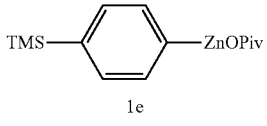 1e | 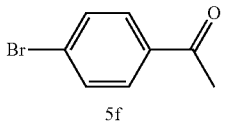 5f | 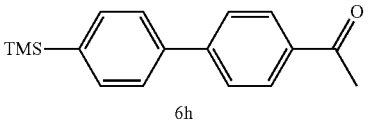 [SMILES: CC(=O)c1ccc(-c2ccc([Si](C)(C)C)cc2)cc1] 6h | 2 h, 25° C., THF | 83 |
| 9 | 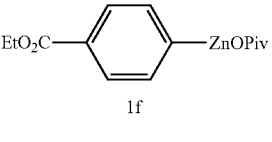 1f | 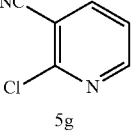 5g | 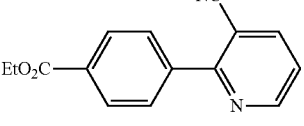 6i | 2 h, 25° C., THF | 84 |
| 10 | 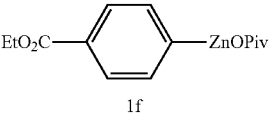 1f | 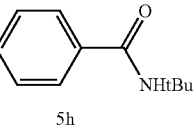 5h | 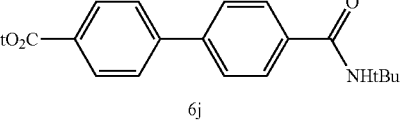 6j | 2 h, 25° C., THF | 87 |
| 11 | 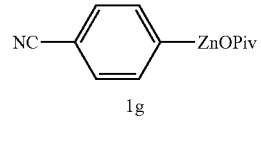 1g | 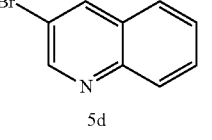 5d | 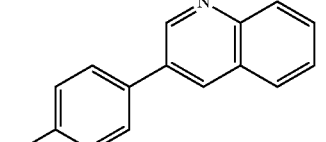 6k | 2 h, 25° C., THF | 88 |
| 12 | 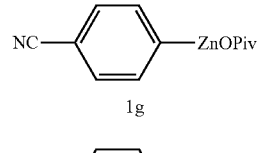 1g | 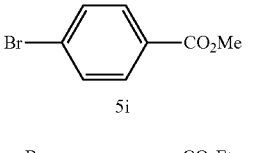 5i | 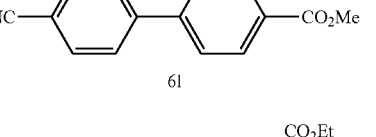 6l | 2 h, 25° C., THF | 81 |
| 13 | 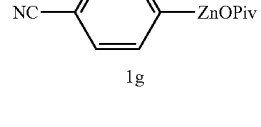 1g | 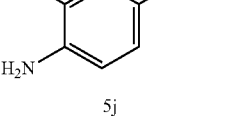 5j | 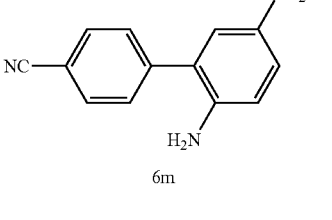 6m | 2 h, 25° C., THF | 56 |
| 14 | 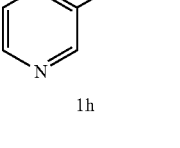 1h | 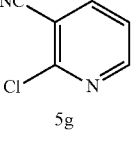 5g | 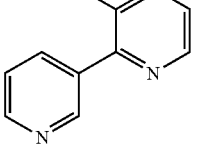 6n | 3 h, 50° C., THF | 91 |
| 15 | 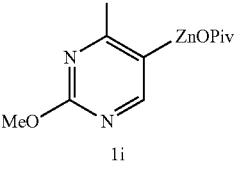 1i | 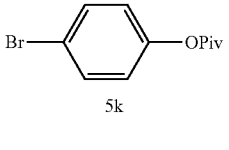 5k | 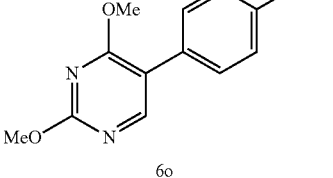 6o | 3 h, 50° C., THF | 80 |

TABLE 3-continued
Negishi-cross-coupling reactions of solid organozinc complexes with various electrophiles
| Entry No. | Organozinc Complex[a] | Electrophile | Product | Time, Temperature, Solvent | Yield [%][b] |
|---|---|---|---|---|---|
| 16 | 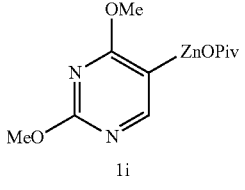 1i | 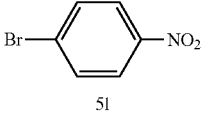 5l | 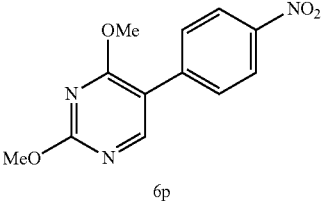 [SMILES: COc1ncc(-c2ccc([N+](=O)[O-])cc2)c(OC)n1] 6p | 3 h, 50° C., THF | 71 |
| 17 | 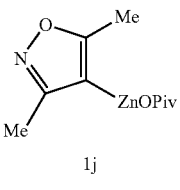 1j | 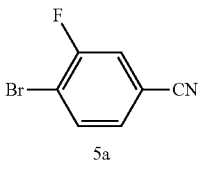 5a | 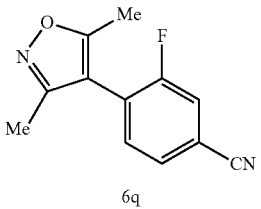 6q | 2 h, 50° C., THF | 99 |
| 18 | 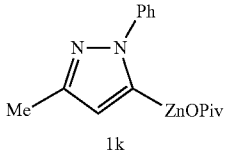 1k | 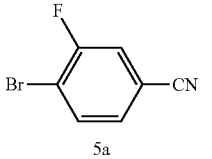 5a | 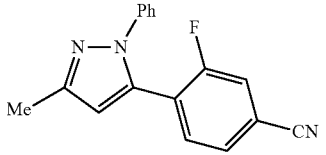 6r | 2 h, 50° C., THF | 97 |
| 19 | 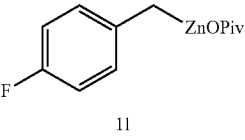 1l | 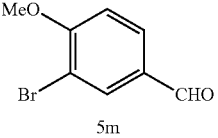 [SMILES: COc1ccc(C=O)cc1Br] 5m | 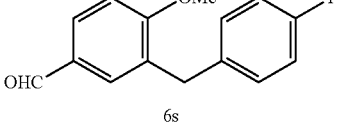 6s | 2 h, 25° C., THF | 82 |
| 20 | 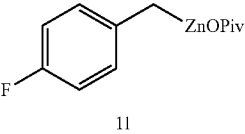 1l | 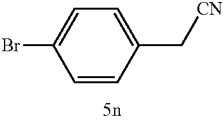 5n | 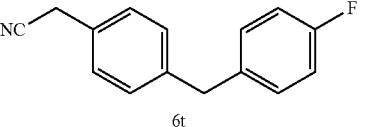 [SMILES: N#CCc1ccc(Cc2ccc(F)cc2)cc1] 6t | 2 h, 25° C., THF | 78 |
| 21 | 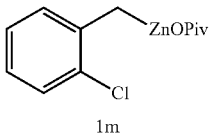 1m | 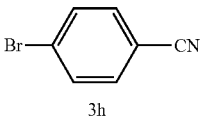 3h | 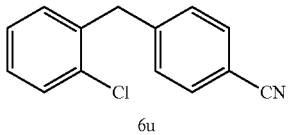 [SMILES: N#Cc1ccc(Cc2ccccc2Cl)cc1] 6u | 2 h, 25° C., THF | 70 |
| 22 | 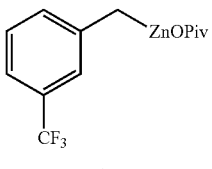 1n | 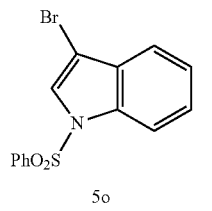 5o | 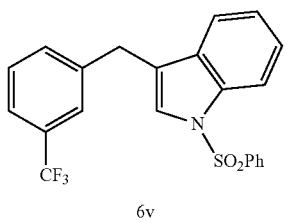 6v | 2 h, 25° C., THF | 86 |

TABLE 3-continued

Negishi-cross-coupling reactions of solid organozinc complexes with various electrophiles

| Entry No. | Organozinc Complex[a] | Electrophile | Product | Time, Temperature, Solvent | Yield [%][b] |
|---|---|---|---|---|---|
| 23 | 1n | 5j | 6w | 2 h, 25° C., THF | 66 |
| 24 | 1o | 5o | 6x | 2 h, 25° C., THF | 78 |
| 25 | 1o | 3j | 6y | 2 h, 25° C., THF | 55 |
| 26 | 1t | 3h | 6z | 12 h, 50° C., THF/NMP (3:1) | 80 |
| 27 | 1u | | 6aa | 12 h, 22° C., THF | 79 |
| 28 | 1f | 5g | 6ab | 12 h, 22° C., AcOEt | 96 |
| 29 | 1f | 5o | 6ac | 12 h, 22° C., AcOEt | 99 |

TABLE 3-continued

Negishi-cross-coupling reactions of solid organozinc complexes with various electrophiles

| Entry No. | Organozinc Complex[a] | Electrophile | Product | Time, Temperature, Solvent | Yield [%][b] |
|---|---|---|---|---|---|
| 30 | EtO$_2$C—C$_6$H$_4$—ZnOPiv (1f) | Br—C$_6$H$_4$—CO$_2$Et (3f) | NC—C$_6$H$_4$—C$_6$H$_4$—CO$_2$Et (6ad) | 2 h, 25° C., AcOEt | 94 |

[a]Complexed zinc and magnesium salts as well as LiCl were omitted for the sake of clarity.
[b]Isolated yield of analytically pure product.

Furthermore, the reactivity of the organozinc reagents towards aromatic halides with carbonyl functions can be tuned by the presence or absence of the PEPPSI-catalyst. Thus, it is possible to perform a coupling reaction of 4-methoxyphenyl zinc pivalate (3a) with 2-bromobenzaldehyde (5p) at 22° C. in 2h in the presence of 2 mol % of PEPPSI and the corresponding biphenylic aldehyde zc1 can be isolated in 87% yield. In the absence of PEPPSI under the same reaction conditions, 4-methoxyphenyl zinc pivalate (3a) adds to the aldehyde functionality of 5p and the secondary alcohol za1 can be isolated in 72% yield (Scheme VIII, equation 1).

In the same manner, 3-methoxybenzylzinc pivalate (3m) can be coupled with 4-chlorobenzophenone (5q) to form the benzylated benzophenone derivative (zc2) in 72% yield in the presence of 2 mol % of PEPPSI. Repeating the reaction in AcOEt leads to an improved yield of 93%. Without PEPPSI a clean addition reaction to the aldehyde function takes place and the corresponding alcohol derivative za2 can be isolated in 80% yield (Scheme VIII, equation 2).

Scheme VIII: Tuneable reactivity of organozinc reagents towards bromobenzaldehydes.

(1)

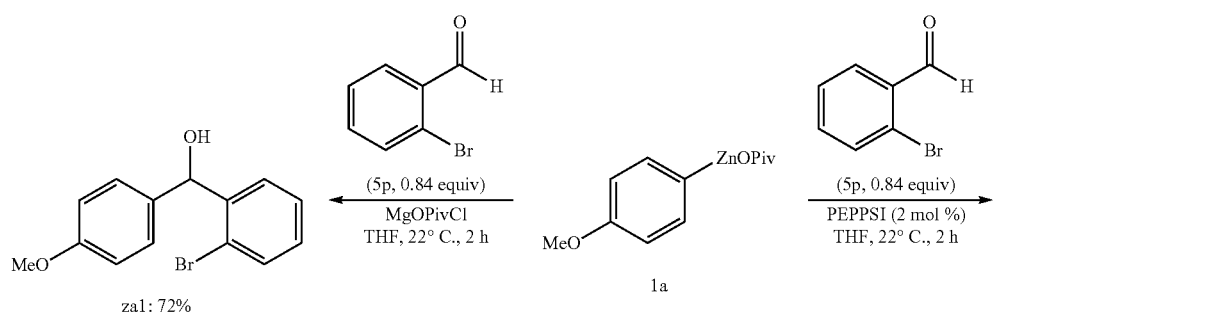

(2)

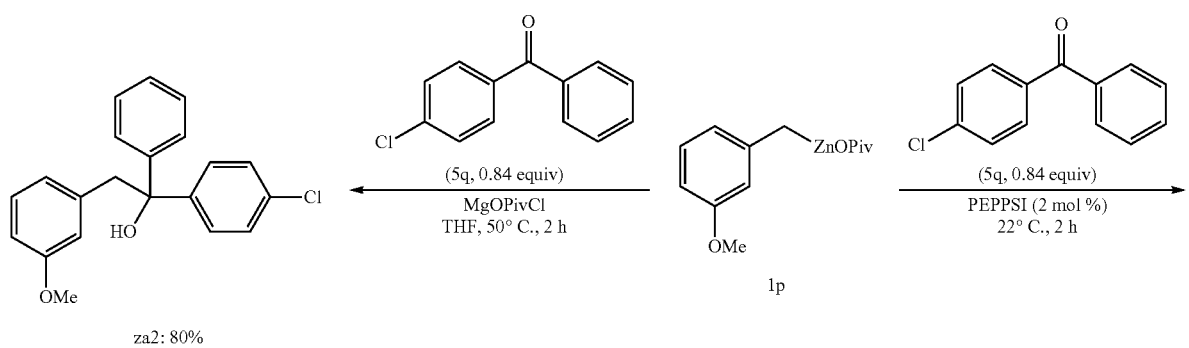

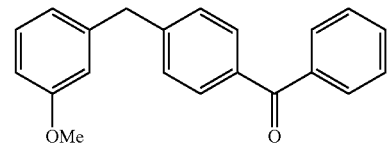

zc2: 72% in THF
93% in AcOEt

These examples show that solid aryl, heteroaryl and benzylic zinc reagents can be prepared by a convenient and cost-efficient magnesium insertion in the presence of Zn(OPiv)$_2$.2LiCl (2) and Zn(O$^t$Bu)$_2$.2LiCl in accordance with this invention. After evaporation of the solvent, the corresponding zinc reagents can be stored as solids under inert gas atmosphere and are sufficiently stable for short term manipulation on air. Furthermore, the solid zinc reagents can be reacted with a broad spectrum of electrophiles in palladium-catalyzed Negishi-cross-coupling reactions. The cross-coupling products are obtained under mild conditions in good to excellent yields. Additionally, the reagents can also be used for addition reactions to carbonyl derivatives.

What is claimed is:
1. A process for making organozinc reagents comprising:
   (1) reacting (A) at least one organomagnesium complex or organozinc complex with (B) at least one coordinating compound comprising one or more carboxylate groups and/or alcoholate groups and/or tertiary amine groups, optionally in combination with zinc ions and/or lithium ions and/or halide ions, wherein the halide ions are selected from chloride, bromide and iodide, the organozinc complex comprises an aryl group, a heteroaryl group or a benzyl group when the coordinating compound is a chelating polyamine, and the reaction is conducted in the presence of zinc complexed with at least one coordinating compound when reactant (A) comprises at least one organomagnesium complex or
   (2) contacting an organic compound having at least one leaving group with magnesium metal and a zinc coordination complex optionally in the presence of lithium halide, wherein the halide is selected from chloride, bromide and iodide and the zinc coordination complex comprises at least one coordinating compound comprising one or more carboxylate groups and/or alcoholate groups and/or tertiary amine groups or
   (3) transmetalating the product of a magnesium-halogen exchange reaction with ZnX'$_2$, wherein X' represents a halide selected from Cl, Br and I, optionally precipitating the magnesium salts, and then reacting the product with a coordination complex, wherein the coordination complex comprises at least one coordinating compound comprising one or more carboxylate groups and/or alcoholate groups and/or tertiary amine groups and zinc ions and/or lithium ions or
   (4) complexing (A) at least one organomagnesium complex and/or organozinc complex with (B) at least one coordinating compound and evaporating the solvent to obtain a solid organozinc reagent, wherein the reaction is conducted in the presence of zinc complexed with at least one coordinating compound when reactant (A) comprises at least one organomagnesium complex wherein
   the organomagnesium complex of process (1) is made in situ concurrently with the process for making an organozinc reagent in a one-pot procedure and/or
   the organomagnesium complex or organozinc complex of process (1) is made via oxidative addition, halogen-magnesium exchange, or C—H activation and/or
   the organomagnesium complex or organozinc complex comprises one or more functional groups selected from nitriles, nitro, esters, ketones, protected alcohols, protected aldehydes, protected amines and protected amides and/or
   process (1) comprises reacting at least one organozinc complex with at least one coordinating compound, wherein the coordinating compound comprises one or more carboxylate groups and/or alcoholate groups and/or tertiary amine groups, wherein the coordinating compound is lithium pivalate or lithium tert-butoxylate.

2. The process according to claim 1, wherein the coordinating compound is represented by formula (I):

$$R^1T_q \quad (I)$$

wherein
each T independently represents —CO$_2^-$, —O$^-$, or —NR'R", wherein each R' and R" independently represent a hydrocarbyl group having from 1 to 6 carbon atoms, which may optionally further comprise one or more hetero atoms, wherein the hetero atoms are not protonated, or R' and R" may be joined together to form a substituted or unsubsituted five- or six-membered heterocyclic ring with the nitrogen atom of —NR'R",
R$^1$ represents an organic residue comprising one or more carbon atoms and, optionally, one or more hetero atoms, wherein the organic residue does not comprise protonated O, N, or S, and
"q" represents a positive integer.

3. The process according to 2, wherein when T represents —O$^-$ or —NR'R", "q" is at least 2.

4. The process according to claim 2, wherein R$^1$ represents a branched aliphatic group having from 4 to 8 carbon atoms.

5. The process according to claim 1, wherein the organomagnesium complex or organozinc complex comprises one or more functional groups selected from nitriles, nitro, esters, ketones, protected alcohols, protected aldehydes, protected amines and protected amides and the functional groups are maintained in the organozinc reagent produced by the process.

6. The process according to 2, wherein the zinc coordination complex is represented by the Formula (IA):

$$R^1T*Zn*TR^1 \quad (IA)$$

wherein T and R$^1$ are defined as in Formula (I).

7. The process according to claim 1, wherein the process is conducted with an organomagnesium complex and the zinc coordination complex comprises lithium halide.

8. The process according to claim 1, wherein the process for making organozinc reagents is conducted substantially in the absence of magnesium.

9. The process according to claim 1, wherein the process is conducted in an organic solvent optionally comprising coordinating solvent and the organic solvent is removed after producing the organozinc reagent until the organozinc complex is isolated from the solvent as a solid residue.

10. A zinc coordination complex comprising a zinc ion, at least one coordinating compound comprising one or more carboxylate groups and/or tertiary amine groups, a lithium ion, and a halide ion, wherein the halide is chloride, bromide or iodide.

11. The zinc coordination complex of claim 10, wherein the coordinating compound is represented by formula (I):

$$R^1T_q \qquad (I)$$

wherein
each T independently represents —CO$_2^{31}$ or —NR'R", wherein each R' and R" independently represent a hydrocarbyl group having from 1 to 6 carbon atoms, which may optionally further comprise one or more hetero atoms, wherein the hetero atoms are not protonated, or R' and R" may be joined together to form a substituted or unsubsituted five- or six-membered heterocyclic ring with the nitrogen atom of —NR'R", R$^1$ represents an organic residue comprising one or more carbon atoms and, optionally, one or more hetero atoms, wherein the organic residue does not comprise protonated O, N, or S, and "q" represents a positive integer.

12. The zinc coordination complex of claim 11, wherein R$^1$ is —C(CH$_3$)$_3$.

13. An organozinc reagent composition comprising (a) at least one organozinc compound complexed with at least one coordinating compound comprising one or more carboxylate groups and/or alcoholate groups and/or tertiary amine groups, (b) optionally magnesium ions, optionally (c) lithium ions, and optionally (d) halide ions, wherein the halide is selected from chloride, bromide and iodide and the organozinc compound comprises an aryl group, a heteroaryl group or a benzyl group, wherein the coordinating compound is represented by formula (I):

$$R^1T_q \qquad (I)$$

wherein
each T independently represents —CO$_2^-$, —O$^-$, or —NR'R", wherein each R' and R" independently represent a hydrocarbyl group having from 1 to 6 carbon atoms, which may optionally further comprise one or more hetero atoms, wherein the hetero atoms are not protonated, or R' and R" may be joined together to form a substituted or unsubsituted five- or six-membered heterocyclic ring with the nitrogen atom of —NR'R", R$^1$ represents an aliphatic group, and "q" represents a positive integer, provided that when T represents —O$^-$or —NR'R", "q" is at least 2.

14. The composition of claim 13, wherein the organozinc compound comprises aryl, heteroaryl or benzyl having one or more functional group substituents.

15. The composition of claim 14, wherein the functional group substituents include functional groups selected from nitriles, nitro, esters and ketones.

16. The composition according to claim 13 comprising Li$^+$and at least one halide selected from chloride, bromide and iodide.

17. The composition according to claim 13, wherein the composition is in a solid form.

18. A process for making organic compounds comprising:
(1) reacting nucleophilic leaving group-substituted organic compound with an organozinc compound in the presence of (a) magnesium ions, (b) at least one coordinating compound comprising one or more carboxylate groups and/or alcoholate groups and/or tertiary amine groups, and (c) a cross-coupling catalyst or
(2) reacting an aldehyde- and/or ketone-substituted organic compound with an organozinc compound in the presence of (a) magnesium ions and (b) at least one coordinating compound, which is not an organozinc compound, comprising one or more carboxylate groups and/or alcoholate groups and/or tertiary amine groups in the absence of a cross-coupling catalyst to form the organic compound via an aldehyde and/or ketone addition reaction.

19. The process according to process (1) of claim 18, wherein the nucleophilic leaving group-substituted organic compound reactant further comprises one or more aldehyde and/or ketone substituents which are retained in the product of the reaction.

* * * * *